(12) United States Patent
Babayoff

(10) Patent No.: US 7,698,068 B2
(45) Date of Patent: Apr. 13, 2010

(54) METHOD FOR PROVIDING DATA ASSOCIATED WITH THE INTRAORAL CAVITY

(75) Inventor: Noam Babayoff, Rishon le Zion (IL)

(73) Assignee: Cadent Ltd., Or Yehuda (IL)

( * ) Notice: Subject to any disclaimer, the term of this patent is extended or adjusted under 35 U.S.C. 154(b) by 809 days.

(21) Appl. No.: 11/154,523

(22) Filed: Jun. 17, 2005

(65) Prior Publication Data

US 2005/0283065 A1 Dec. 22, 2005

Related U.S. Application Data

(60) Provisional application No. 60/580,109, filed on Jun. 17, 2004, provisional application No. 60/580,108, filed on Jun. 17, 2004.

(51) Int. Cl.
 *G01N 33/48* (2006.01)
 *A61C 9/00* (2006.01)
 *A61B 5/103* (2006.01)

(52) U.S. Cl. .............................. 702/19; 433/37; 600/589

(58) Field of Classification Search .................... 702/19, 702/1; 433/1, 2, 24, 26, 29, 37, 213, 45, 433/191, 196, 199.1, 201.1, 202.1, 203.1; 382/128, 277, 278, 286, 291; 356/456, 485, 356/490, 496; 600/587, 589, 590, 407; 700/90, 700/95, 117, 118; 623/90
See application file for complete search history.

(56) References Cited

U.S. PATENT DOCUMENTS

| 4,836,674 A | 6/1989 | Lequime et al. ............. 356/319 |
| 5,417,572 A | 5/1995 | Kawai et al. ................. 433/218 |
| 5,431,562 A * | 7/1995 | Andreiko et al. ............... 433/24 |
| 5,743,730 A | 4/1998 | Clester et al. .................. 433/26 |
| 5,766,006 A | 6/1998 | Murljacic ..................... 433/26 |
| 5,800,164 A | 9/1998 | Pfau ........................... 433/26 |
| 5,851,113 A | 12/1998 | Jung et al. .................... 433/29 |
| 5,871,351 A | 2/1999 | Jung et al. .................... 433/29 |
| 6,007,332 A | 12/1999 | O'Brien ....................... 433/26 |
| 6,030,209 A | 2/2000 | Panzera et al. ................. 433/26 |

(Continued)

FOREIGN PATENT DOCUMENTS

DE 199 22 870 A1 12/2000

(Continued)

OTHER PUBLICATIONS

Yamany et al., A 3-D Reconstruction System for the Human Jaw Using a Sequence of Optical Images, May 2000, IEEE Transactions on Medical Imaging, vol. 19, No. 5, pp. 538-547.*
Int'l Search Report.

*Primary Examiner*—Edward R Cosimano
*Assistant Examiner*—Toan M Le
(74) *Attorney, Agent, or Firm*—The Nath Law Group; Derek Richmond; Sung Yeop Chung

(57) ABSTRACT

A method for providing data useful in procedures associated with the oral cavity, in which at least one numerical entity representative of the three-dimensional surface geometry and color of at least part of the intra-oral cavity is provided and then manipulated to provide desired data therefrom.

30 Claims, 18 Drawing Sheets

U.S. PATENT DOCUMENTS

| | | | |
|---|---|---|---|
| 6,033,222 A | 3/2000 | Schneider, II et al. | 433/203.1 |
| 6,118,521 A | 9/2000 | Jung et al. | 356/73 |
| 6,190,170 B1 | 2/2001 | Morris et al. | 433/215 |
| 6,238,567 B1 | 5/2001 | Van de Moortele | 210/670 |
| 6,239,868 B1 | 5/2001 | Jung et al. | 356/73 |
| 6,246,479 B1 | 6/2001 | Jung et al. | 356/419 |
| 6,379,593 B1 | 4/2002 | Datzmann et al. | 264/20 |
| 6,409,504 B1 * | 6/2002 | Jones et al. | 433/24 |
| 6,417,917 B1 | 7/2002 | Jung et al. | 356/73 |
| 6,525,819 B1 | 2/2003 | Delawter et al. | 356/406 |
| 6,538,726 B2 | 3/2003 | DeJung et al. | 356/73 |
| 6,570,654 B2 | 5/2003 | Jung et al. | 356/419 |
| 6,573,984 B2 | 6/2003 | Jung et al. | 356/73 |
| 6,621,491 B1 * | 9/2003 | Baumrind et al. | 345/419 |
| 6,739,869 B1 | 5/2004 | Taub et al. | 433/24 |
| 6,819,318 B1 * | 11/2004 | Geng | 345/420 |
| 6,957,118 B2 * | 10/2005 | Kopelman et al. | 700/118 |
| 7,110,594 B2 * | 9/2006 | Jones et al. | 382/154 |
| 7,110,844 B2 * | 9/2006 | Kopelman et al. | 700/118 |
| 7,296,996 B2 * | 11/2007 | Sachdeva et al. | 433/24 |
| 7,383,094 B2 * | 6/2008 | Kopelman et al. | 700/118 |
| 2001/0002310 A1 | 5/2001 | Chishti et al. | 433/24 |
| 2003/0026469 A1 | 2/2003 | Kreang-Arekul et al. | 382/132 |
| 2003/0219148 A1 | 11/2003 | Scharlack et al. | 382/128 |
| 2004/0029068 A1 | 2/2004 | Sachdeva et al. | 433/24 |

FOREIGN PATENT DOCUMENTS

| | | |
|---|---|---|
| EP | 0 360 657 A1 | 3/1990 |
| EP | 1 252 867 A1 | 10/2002 |
| WO | 00/08415 | 2/2000 |
| WO | 2004/008981 A2 | 1/2004 |
| WO | 2004/008981 A3 | 1/2004 |

* cited by examiner

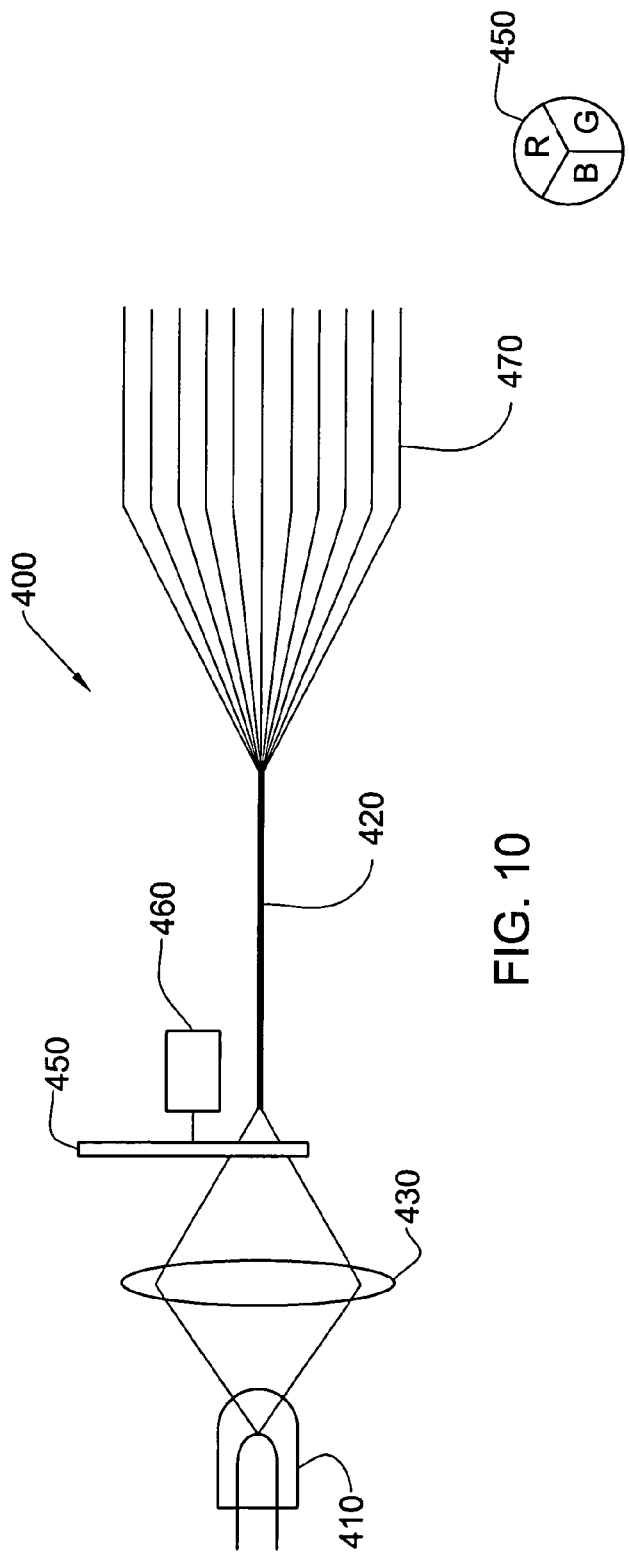
FIG. 10A
FIG. 10
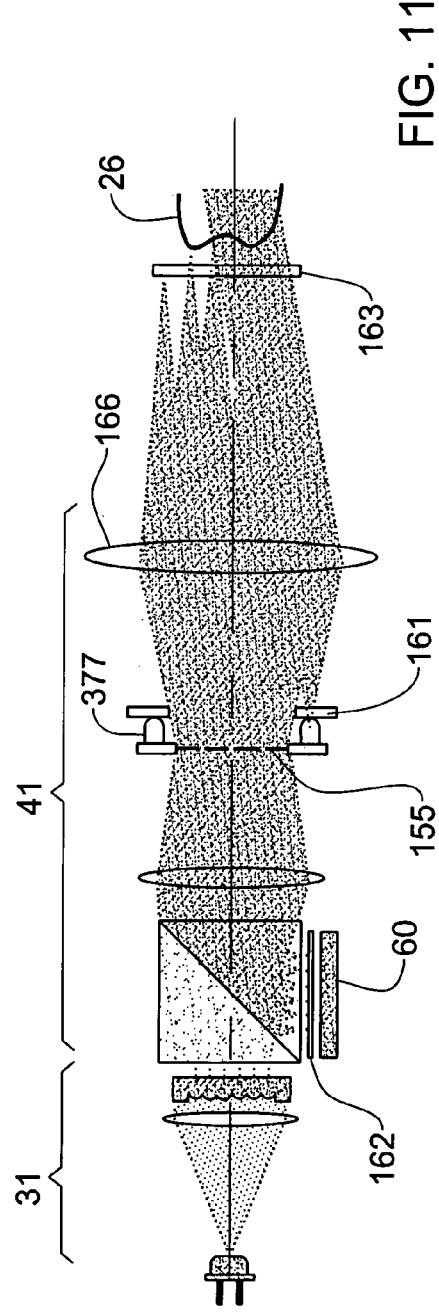
FIG. 11

METHOD FOR PROVIDING DATA ASSOCIATED WITH THE INTRAORAL CAVITY

CROSS-REFERENCE TO RELATED APPLICATIONS

This application claims benefit of prior U.S. Provisional Patent Application No. 60/580,109, filed Jun. 17, 2004, and U.S. Provisional Patent Application No. 60/580,108, filed Jun. 17, 2004, the contents of which are hereby incorporated by reference in their entirety.

FIELD OF THE INVENTION

The present invention relates to color three-dimensional numerical entities representative of tissues, particularly of the intraoral cavity. In particular, the present invention is concerned with the manipulation of such entities to provide data that is useful in procedures associated with the oral cavity, specially dental surfaces thereof.

BACKGROUND OF THE INVENTION

There are many procedures associated with the oral cavity in which a precise three-dimensional representation of the cavity is very useful to the dental practitioner. Herein, "practitioner" refers to any one of a dentist, dental surgeon, dental technician, orthodontist, prosthodontist, or any other caregiver that may be involved in determining, preparing or providing dental treatment to a patient, particularly orthodontic treatment.

Such representations enable the practitioner to study the cavity of individual patients in a similar manner to the study of the traditional plaster model. More importantly, three-dimensional numerical entities of the dental cavity also allow the practitioner to study alternative methods or approaches when dealing with particular dental problems of any given patient. For example, in orthodontics, a computer model of a patient's teeth may be manipulated to arrive at the optimal arrangement for brackets to ensure effective treatment of crooked teeth. For such procedures, it is often useful to provide a three-dimensional representation of the individual teeth, each of which can be moved independently in a computer simulation of the orthodontic treatment plan and orthodontic record. Hitherto, identification and separation of the data sets representative of the individual teeth has been performed manually.

In U.S. Pat. No. 6,739,869, assigned to the present Assignee, a method for virtual orthodontic treatment is disclosed in which a virtual set of orthodontic components is associated, in a virtual space, with a first virtual three-dimensional image of teeth, and then by a set of rules which define the effect of the set of components' teeth, the effect of the virtual treatment can be computed. This virtual treatment can be used to predict the results of a real-life orthodontic treatment as to design such a treatment.

Another procedure relates to the manufacture of a dental prosthesis, such as a crown or bridge, which requires the finish line, or transition boundary between the prosthesis and the dental preparation to be precisely defined in three-dimensions. Obtaining the finish line coordinates from a computer model is more efficient and often more accurate than from a plaster cast, and moreover facilitates the production of such a prosthesis, for example via CNC machining, rapid prototyping, or other computerised technologies, if desired.

There are also procedures in which particularly good three-dimensional definition of a large area of the intraoral cavity is required, and it may be necessary at times to scan parts of the cavity sequentially and then "stitch" the various data sets together. Thus, surface topologies of adjacent portions, at times from two or more different angular locations relative to the structure, are determined and the topologies are combined, in a manner known per se. In practice, such stitching is usually performed automatically, by identifying a surface profile or topography corresponding to at least part of the data of one data set that is substantially identical to that of another data set. The data sets are then manipulated such as to match the coordinates of the surface profile between the data sets to obtain a larger numerical entity comprising these data sets in their proper spatial relationship. However, the data sets often include surface data relating to the soft tissues such as gums, cheeks and tongue, for example, which may distort and move while the different scans are performed. This relative movement makes the stitching procedure more problematic, since parts of the data sets thus obtained will never synchronise, even though they relate to overlapping portions of the intraoral cavity.

In procedures relating to the manufacture of a dental prosthesis such as a crown or bridge, or in other dental restorations, it is important to match the color and texture of the prosthesis with that of the surrounding teeth in the vicinity of the target area in which the prosthesis is to be implanted, to give the prosthesis or restoration a natural appearance. Traditional methods of color matching are based on visual comparison between a removable tooth-shaped color tab of a shade guide, such as for example Vita, and the surrounding teeth. The practitioner can then choose the standard shade that best matches the overall color of the other teeth. The appropriate shade reference can then be communicated to the laboratory that is to manufacture the prosthesis. Similar matching methods are routinely employed for enabling the color of filler material to be matched to the tooth that requires a filling. It should be noted that unlike the tooth shades from the shade guides, which are uniform in color, a tooth have many different shades. For example, tooth stains and the like alter then tooth's color locally. Attempts have been made at providing a more exact match. For example in U.S. Pat. No. 5,800,164 a system is described for the selection of form and color structure of teeth, and includes several assortments of models and representations as well as layering diagrams of different tooth forms and color structures. A comparison of form and color structure between the patient's teeth and the models is made, and a suitable assortment is selected. The layering diagrams thus produced enable the production of the prosthesis to be carefully controlled to provide the desired form and color structure. In U.S. Pat. No. 4,836,674 a method and apparatus are described for obtaining the best color match with respect to adjacent teeth, for different lighting conditions, but considers only the overall color of the teeth, and does not address local variations of color in the teeth. In U.S. Pat. No. 6,525,819, a calorimeter is provided for providing, inter alia, the one-dimensional array of color data along a line on the surface of the intra-oral cavity, including the teeth. In U.S. Pat. No. 5,766,006 a method is described for comparing the tooth shade after the patient's teeth are whitened, in which a color two-dimensional image of the tooth is obtained before the whitening, comparing the color information representative of the color of the tooth, and identifying one or more tooth shades with a combined color corresponding to the color of the tooth. After whitening the tooth, another image is taken thereof and compared to the image before whitening.

Other US patents of general background interest include the following.

In U.S. Pat. Nos. 5,851,113, 5,871,351, 6,118,521, 6,239,868, 6,246,479, 6,417,917, 6,538,726, 6,570,654 and 6,573,984 color measuring systems and methods such as for determining the color or other characteristics of teeth are disclosed, in which these characteristics are obtained using a fibre optics arrangement which is targeted onto a specific area of each tooth and at a certain height and angle with respect to this area. The color measurement data obtained may be used to implement processes for forming dental prostheses.

In U.S. Pat. No. 6,007,332, a method and system for determining the color characteristic of a tooth employs the photographic imaging of the tooth, and the photographing of visually selected color standards, to achieve the final selection of the closest color match. The resulting photographic images, which may be on a single photograph, are subjected to calorimetric or spectrophotometric analysis to achieve the final selection of the closest match.

In U.S. Pat. No. 6,030,209, a spectrophotometer device measures and provides general colorimetric data regarding hue, chroma, value, and translucency for each of the incisal, middle, and cervical regions of the tooth. This calorimetric data is then converted via an algorithm to a recipe that the dentist or dental technician follows in constructing a dental restoration. A porcelain system is also provided which allows a user to independently alter one color component while not affecting the other three color components.

In U.S. Pat. No. 6,033,222, a fabrication method for dental translucent restorations involves forming a dental die from impression of tooth stump, in which a series of die spacers of differing shades are used to match or replicate an assortment of tooth stump or dentin tooth shades. The method comprises applying color and shade to match dentist's prescription, forming a dental wax-up and then the dental structure.

In U.S. Pat. Nos. 6,190,170, and 6,238,567, an automated tooth shade analysis and matching method is used for making a dental prosthesis. An image of the teeth is acquired including black and white normalization references for determining absolute black and absolute white within the image. The image is normalized in accordance with the normalization references, and then standardized by matching the pixels of the normalized image to selected shade standards for the prosthesis.

In U.S. Pat. No. 6,379,593, a method for producing a multi-colored dental restoration is disclosed. A compacting die is filled with a matrix of two or more plastics materials of different colors, and the pressure is applied to the matrix in the die.

The 3D surface structure of the teeth is not considered in any of the aforesaid patents.

SUMMARY OF THE INVENTION

"Color" is used herein to refer to a perceived optical characteristic, including one or more of the following: hue, chroma, value, translucency, reflectance.

"Hue" is used herein to refer to a color or to the name of a color, for example primary or other colors such as red, green, blue, violet, green and so on, or to combination of colors, such as for example yellowish green. The hues of primary interest herein include red, and shades of white including yellow for intraoral cavity tissues, and other hues representative of the color of filings and so on.

"Chroma" is used herein to refer to strength, intensity or saturation of the hue.

"Value" is used herein to refer to the brightness of a color.

"Translucency" is used herein to refer to quality of transmitting and diffusing light, generally ranging from opaque to transparent.

"Reflectance" is used herein to refer to the quality of reflecting light incident on the tooth.

"Numerical entity" is used herein to mean a data set or to a set of instructions that is manipulable by automated numerical processing means, such as a computer for example, particularly such that specific data may be obtained therefrom.

Such manipulation may be under manual, interactive, partial or fully automated control.

The present invention is directed to a method of providing data useful in procedures associated with the oral cavity comprising:

providing at least one numerical entity representative of the three-dimensional surface geometry and color of at least part of the intra-oral cavity; and manipulating said entity to provide desired data therefrom.

Typically, the numerical entity comprises surface geometry and color data associated with said part of the intra-oral cavity, and the color data includes actual or perceived visual characteristics including hue, chroma, value, translucency, reflectance.

In an first embodiment, particularly useful for differentiating a first tissue from a second tissue, wherein said first tissue comprises substantially different color characteristics from those of said second tissue, comprises separating said surface geometry and color data into at least two tissue data sets, wherein a first said tissue data set comprises surface geometry and color data, wherein said color data thereof is correlated with a color representative of said first tissue; and a second said tissue data set comprises surface geometry and color data, wherein said color data thereof is correlated with a color representative of said second tissue.

The first tissue comprises hard tissues such as teeth, and the soft tissue comprises at least one of gums, tongue, cheeks and lips.

The first tissue data set may correspond to a plurality of teeth of said intraoral cavity, and in the next step the first tissue data set is divided into a plurality of sub data sets, wherein each said sub data set correspond to a different said tooth.

In the next step, the sub data sets may be manipulated in a manner simulating an orthodontic treatment on said teeth.

Optionally, the sub data sets may be displayed as images corresponding to individual teeth.

The first embodiment may also be used for determining the finish line for a dental preparation.

The second embodiment is particularly useful for stitching at least two said entities, wherein at least a portion of said entities comprise overlapping spatial data, comprising:—

(a) for each entity providing at least one sub entity comprising a first tissue data set comprising surface geometry and color data, wherein said color data thereof is correlated with a color representative of a first tissue; and (b) stitching said first tissue data sets together based on registering portions of said data set comprising said overlapping spatial data.

The first tissue may comprise hard tissues of the intraoral cavity, such as for example teeth.

Optionally, the method may further comprise the step of:

for each entity separating said surface geometry and color data into a second tissue data set, comprising surface geometry and color data, wherein said color data thereof is correlated with a color representative of a second tissue.

The second tissue typically comprises the soft tissues of the intraoral cavity, including at least one of gums, tongue, cheeks and lips.

In one variation of the method, step (b) comprises:

providing coarse stitching of the original entities of step (a) by registering overlapping spatial data thereof to determine coarse spatial relationships between said entities;

applying said coarse spatial relationships to said first tissue data sets to facilitate registration of overlapping portions; and stitching said first tissue data sets together based on registering said overlapping portions.

By eliminating the data associated with the soft tissues, and proceeding with stitching only the hard tissues using the color data, the quality of the stitching procedure is significantly better than when using the full intra-oral data for the stitching procedure.

A third embodiment is particularly useful for providing a finish line for a preparation area in said intraoral cavity, though it may also be used for virtually separating the teeth from the gums. The method comprises:—

(a) comparing the color data for each pair of spatially adjacent data points in said numerical entity;

(b) if the color data for said pair of data points are substantially different one from the other, providing one said data point of said pair of data points; and (c) applying a search algorithm for identifying said finish line in said numerical entity, wherein said application of said algorithm is initially applied to a part of said entity corresponding to the said provided data points of step (b).

Optionally, in step (b) the data point of said pair of data points having color data associated with a hard tissue is provided for step (c).

In a fourth embodiment of the invention, the color data associated with at least one tooth of said intraoral cavity is used for providing shading data for a prosthesis for use in said intraoral cavity.

The method typically includes the steps:

(a) providing separate numerical sub-entities each associated with a different one of at least one tooth within said intra-oral cavity;

(b) providing a prosthesis entity comprising surface geometrical data, said prosthesis entity being associated with a desired prosthesis;

(c) mapping color data from at least one sub entity in step (a) to said prosthesis entity according to predetermined criteria.

Optionally, step (c) comprises (i) transforming the geometrical data of each said separate numerical sub-entities to correspond to a predetermined geometrical form, and mapping said color data to said geometrical form to provide for each said separate numerical sub-entity a transformed sub-entity;

(ii) transforming the geometrical data in (b) to correspond to said prosthesis entity and mapping color data associated with the transformed sub-entity to said prosthesis entity.

Optionally, in step (a) a single numerical sub-entity associated with one tooth within said intra-oral cavity is provided.

Alternatively, in step (a) a plurality of separate numerical sub-entities associated with a corresponding plurality of teeth within said intra-oral cavity are provided; and wherein in step (c) the said transformed sub-entities are combined to a single transformed sub-entity, wherein color data corresponding to said plurality of numerical sub-entities in (a) are combined in a predetermined manner. Such a predetermined manner comprises averaging the color value at each corresponding data point of said plurality of numerical sub-entities in (a). Optionally, the predetermined manner comprises weight averaging the color value at each corresponding data point of said plurality of numerical sub-entities in (a).

Typically, step (a) comprises:— separating said surface geometry and color data into at least two tissue data sets, wherein a first said tissue data set comprises surface geometry and color data, wherein said color data thereof is correlated with a color representative of said first tissue; and a second said tissue data set comprises surface geometry and color data wherein said color data thereof is correlated with a color representative of said second tissue.

The first tissue comprises hard tissues such as teeth, and the soft tissue comprises at least one of gums, tongue, cheeks and lips.

The first tissue data set may correspond to a plurality of teeth of said intraoral cavity, and in the next step the first tissue data set is divided into a plurality of sub data sets, wherein each said sub data set correspond to a different said tooth.

In another aspect of the present invention, a computer readable medium is provided that embodies in a tangible manner a program executable for providing data useful in procedures associated with the oral cavity. The computer readable medium comprises:

(a) a first set of data representative of the three dimensional surface geometry and color of at least part of the intra oral cavity;

(b) means for manipulating said first data set to provide desired data therefrom.

The medium may comprise, for example, optical discs, magnetic discs, magnetic tapes, and so on.

In another aspect of the invention, a system for carrying out the method of the invention is provided. The system according to this aspect of the invention comprises:

an input utility for receiving data indicative of three dimensional color data of the intraoral cavity, obtained directly using a suitable 3D color scanner (for example the device described herein in reference to FIGS. 1 to 13) or obtained elsewhere and transmitted to the input facility via any communication medium, including for example the internet, an intranet, and so on;

a memory utility for storing the data;

a processor utility for manipulating said first data set to provide desired data therefrom, particularly using any algorithm designed to execute the method of the present invention; and output utility.

System can be connected to any suitable display such as a screen or a printer, for example, for visually presenting the manipulated entities. System can be also connectable to an additional utility such as a virtual treatment system, for example for designing a virtual orthodontic treatment.

BRIEF DESCRIPTION OF THE DRAWINGS

In order to understand the invention and to see how it may be carried out in practice, a preferred embodiment will now be described, by way of non-limiting example only, with reference to the accompanying drawings, in which:

FIG. 10 illustrates an alternative illumination arrangement used with the embodiment of FIG. 8. FIG. 10A illustrates details of the tri-color disc used with the illumination arrangement of FIG. 10.

FIG. 11 illustrates in side view the general arrangement of the main elements used in fifth embodiment of the device of FIG. 1 to provide a two dimensional color entity.

DETAILED DESCRIPTION OF THE INVENTION

The first step of the method according to the present invention relates to providing at least one numerical entity that is representative of the three-dimensional surface geometry and color of at least part of the intra-oral cavity.

The said numerical entity is typically at least "four-dimensional", that is, each data point of the data set comprises at least four prime independent variables. In the preferred embodiments of the invention, three of the prime independent variables relate to spatial coordinates of a surface, typically defined along orthogonal. Cartesian axes, x, y, z. Alternatively, these variables may be defined along polar axes or any other geometric system in which a surface may be described. The fourth prime independent variable refers to a color parameter that is expressed numerically and associated with the spatial coordinates. The color parameter may itself be comprised of independent prime color variables—for example relating to the red, blue and green (RGB) components associated with the color parameter. Alternatively, the color parameter may be expressed in terms of the Hue, Saturation and Intensity (HIS). Alternatively, any other color parameter may be used, including parameters that provide a measure of internal reflectance and translucency, or any other optical property of teeth.

Thus, the numerical entity may comprise a data set of a plurality of 4-dimensional arrays—(x, y, z, c), wherein each array represents the x, y, z, geometrical coordinates and the color c of a point on a surface within the intra-oral cavity.

Any suitable means may be used to provide the numerical entity. For example, a three-dimensional surface scanner with color capabilities may be used. Advantageously, such a scanner makes use of confocal imaging for providing an accurate three-dimensional representation of the target surface within the intra-oral cavity. Color values are then added to each data point of this data set by obtaining a two-dimensional color image of the target surface, and then mapping the color values of the two-dimensional image onto the three-dimensional "image".

The following are examples on how to obtain the 3D color numerical entity.

Figure 1:
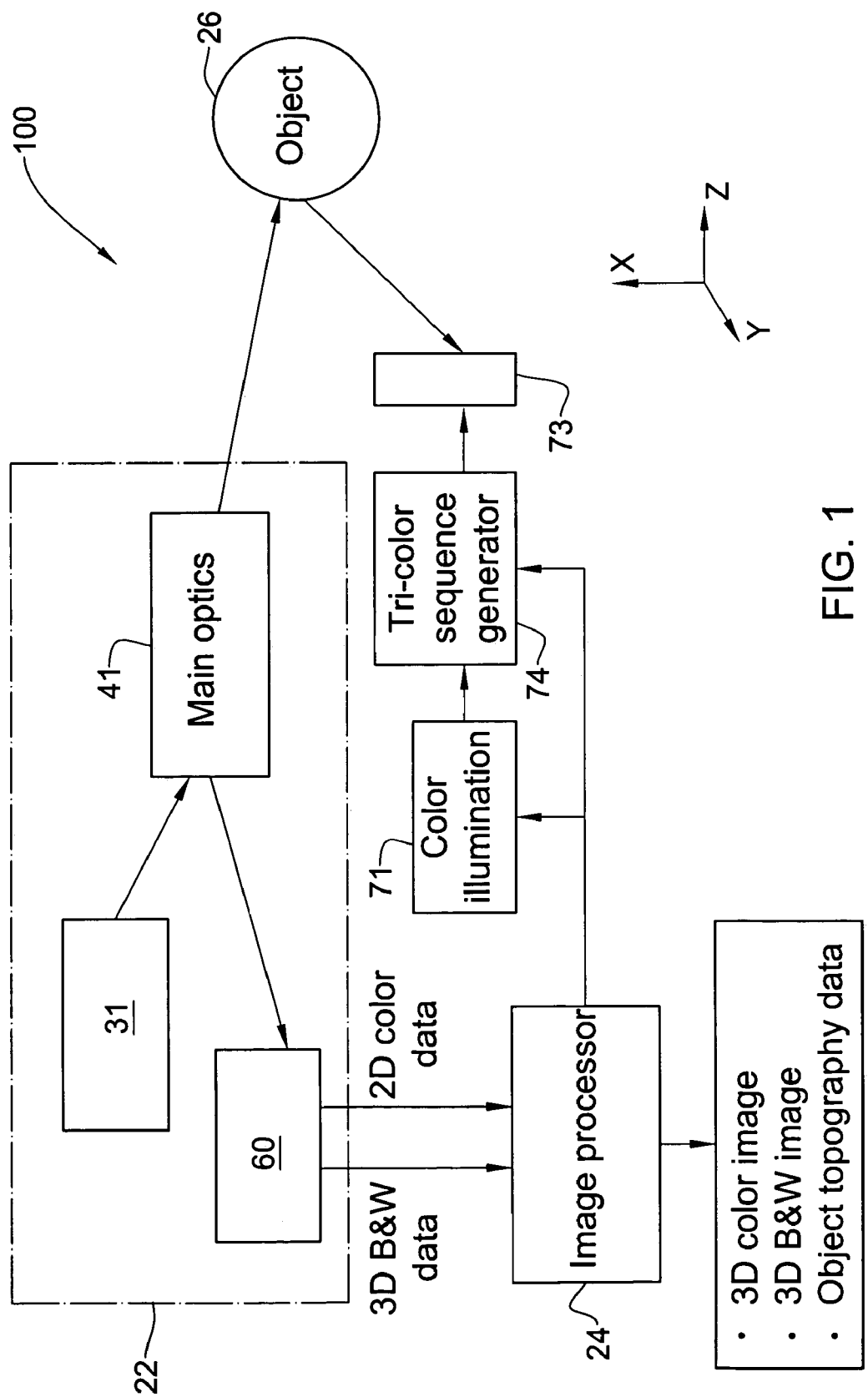
FIG. 1 illustrates the main elements of embodiments of devices for creating a three-dimensional color numerical entity that is manipulated according to the present invention.

Reference is first being made to FIG. 1 which illustrates the general relationship between the various elements of a device for providing a 3D color numerical entity, generally designated with the numeral 100, according to the embodiments of the device described herein.

The device 100 comprises a main illumination source 31 for illuminating the object of interest 26, typically a part of the intraoral cavity, and is optically coupled to main optics 41 to provide depth Z values for an array range of X-Y points (according to a known frame of reference) along the surface of the object 26. Detection optics 60 comprises an image sensor, typically a CCD, that is preferably monochromatic to maximise the resolution of the device, and which typically defines the X-Y frame of reference. Alternatively, the CCD may be adapted to receive color images. The detection optics 60 receives image data from the main optics 41 and the image processor 24 determines the depth Z values for each X-Y point illuminated on the object 26 based on this image data. In this manner, a manipulable three-dimensional numerical entity E comprising the surface coordinates of the object 26.

The device 100 further comprises color illuminating means, such as for example a tri-color sequence generator 74, for selectively illuminating the object 26 with suitable colors, typically Green, Red and Blue, and for each such monochromatic illumination, a two dimensional image of the object 26 is captured by the detection optics 60. The processor 24 then processes the three differently colored monochromatic images and combines the same to provide a full color 2D image of the object. The device 100 is configured for providing color data for an array of X-Y points that is according to the same frame of reference as the X-Y array used for obtaining the 3D entity.

Figure 2A:
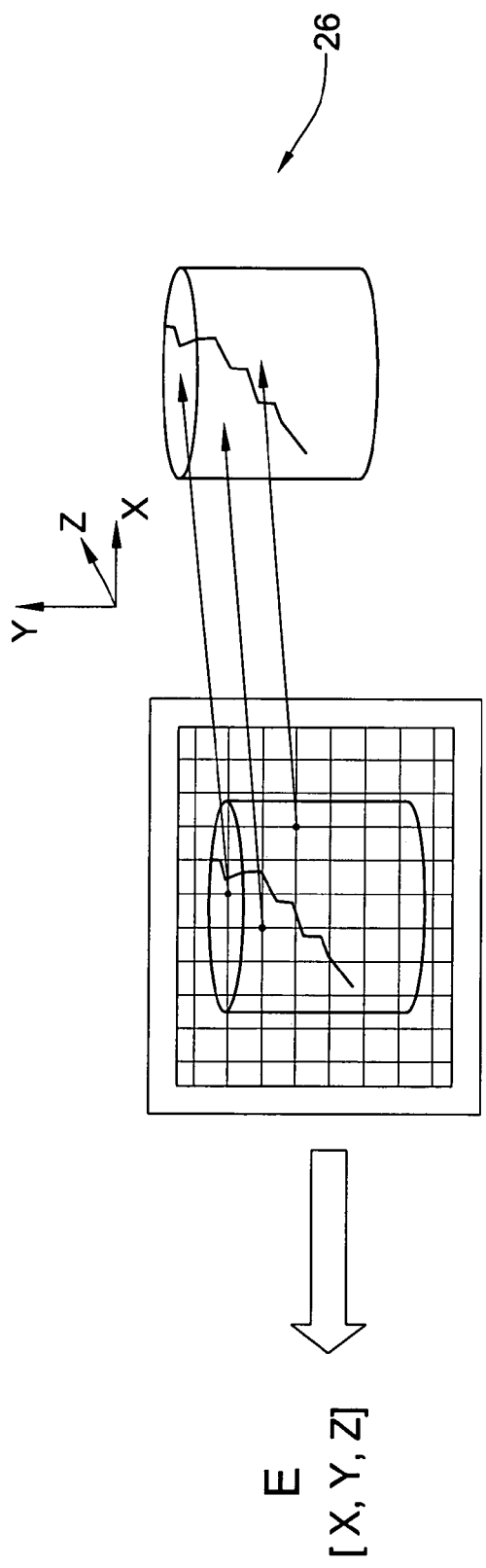
FIGS. 2A, 2B, 2C graphically illustrates the creation of a three dimensional color entity from a three dimensional monochrome entity and a two dimensional color entity.
Figure 2B:
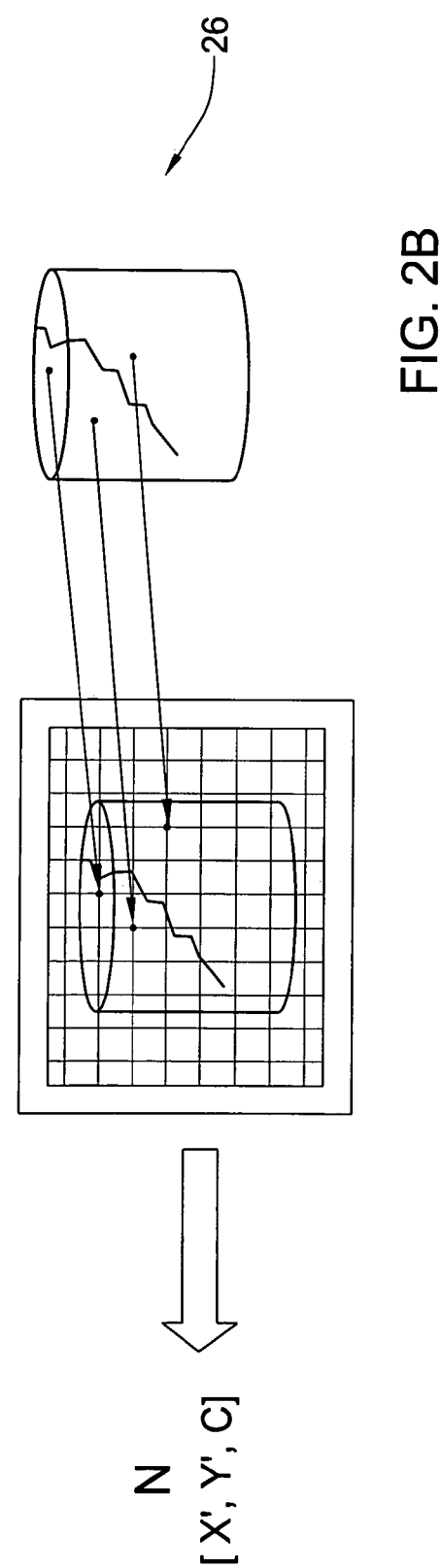
Figure 2C:
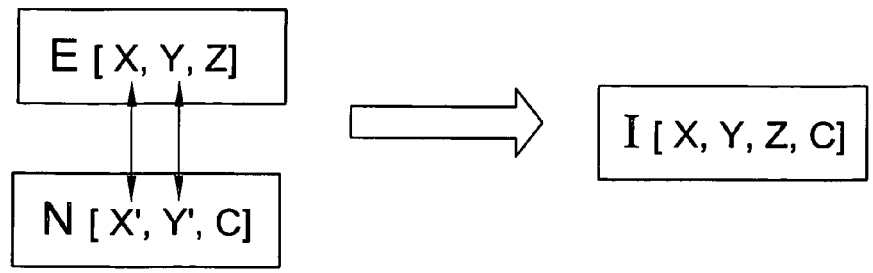

The processor 24 aligns the 2D color image with the 3D entity previously created, and then provides color values to this entity by mapping color values to the entity at aligned X-Y points. Such alignment is straightforward because both the 3D data and the 2D color data are referenced to the same X-Y frame of reference. Referring to FIGS. 2A, 2B, 2C, the mapping procedure is performed as follows. A three-dimensional numerical entity E is obtained by determining depth Z-values for a grid of X-Y points, illuminated via main optics 41 and determined by image processor 24. The entity E thus comprises an array of (X, Y, Z) points, as illustrated in FIG.

2A. The X-Y plane of entity E is substantially parallel to the sensing face of the image sensing means of the detection optics 60, typically a CCD. Almost concurrently, i.e., either just before or just after the readings for determining the 3D entity E are obtained by the detection optics 60, a 2D color image of the object 26 is taken using the same detection optics 60, at substantially the same relative spatial disposition between the detection optics 60 and the object 26, FIG. 2B. If a monochromatic CCD is used, the 2D color image obtained is a composite created from three separate monochromatic images, each provided by illuminating the object 26 with a different color, such as for example red, green and blue. The 2D color image thus corresponds to another entity N comprised of the location and color value of each pixel forming this image, (X', Y', C). The X'-Y' coordinates of the pixels are on a plane substantially parallel to the X-Y plane of the entity E, and furthermore these coordinates represent substantially the same part of the object 26 as the X-Y coordinates of entity E. The reason for this is that the optical information that is used for creating both the 3D entity E and the color 2D entity N are obtained almost simultaneously with a very small time interval therebetween, and typically there is insufficient time for any significant relative movement between the image plane of the detection optics 60 and the object 26 to have occurred between the two scans. Thus, similar X-Y and X'-Y' coordinates in the entities E and N, respectively, will substantially represent the same part of the object 26. Accordingly, the color value C of each pixel of entity N can be mapped to the data point of entity E having X-Y coordinates that are the same as the X'-Y' coordinates of the pixel, whereby to create another entity I comprising surface coordinate and color data, (X, Y, Z, C), as illustrated in FIG. 2C.

Were the relative angle and disposition between the plane of the sensing face of the detection optics 60 with respect to the object 26 change significantly between the 2D and the 3D scans, then the X-Y coordinates of entity E having similar values to the X'-Y' coordinates of entity N could correspond to different parts of the object 26, and thus it may then be difficult to map the color values of entity N to entity E. However, if only a small movement between the detection optics 60 with respect to the object 26 occurs, particularly involving a relative translation or a rotation about the depth direction (Z), but substantially no change in the angular disposition between detection optics 60 and the object 26 about the X or Y axes, it may still be possible to map the color values of entity N to entity E, but first an alignment procedure must be followed.

Figure 3:
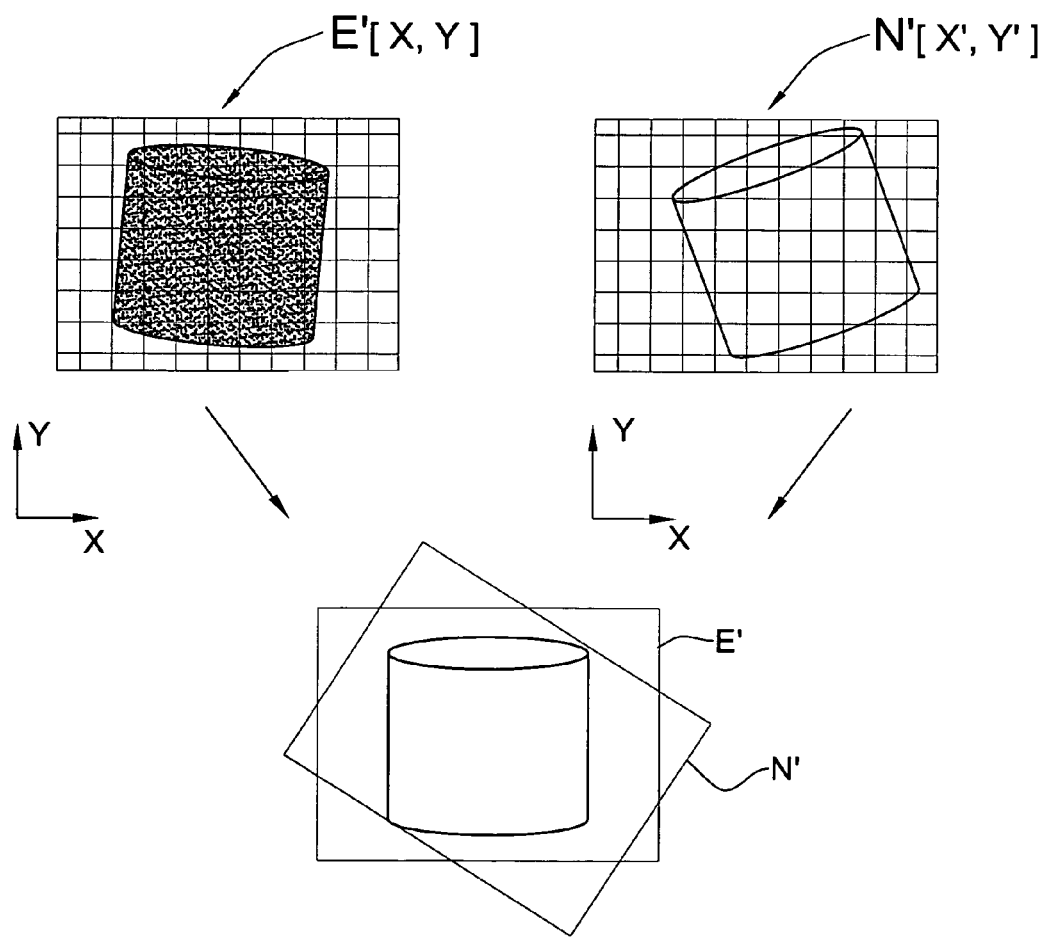
FIG. 3 graphically illustrates an alignment procedure according to the invention for aligning the X-Y coordinates of a three dimensional monochrome entity with corresponding coordinates of a two dimensional color entity.

Referring to FIG. 3, such an alignment procedure may be based on optical character recognition (OCR) techniques. In the X-Y plane, the X-Y coordinates of entity E can be divided up into two groups, one group comprising Z values corresponding to the depth of the object, and a second group for which no reasonable Z value was found, and this group corresponds to the background relative to object 26. The profiles of shapes represented by the X-Y coordinates of the first group of entity E, herein referred to as another entity E', are then optically compared with profiles of shapes corresponding to the X'-Y' coordinates of entity N, herein referred to as another entity N'. Accordingly, entity E' is translated or rotated (coplanarly) with respect to entity N' until a best fit between the optical shapes between the two entities is obtained, using OCR techniques that are well known in the art. Typically, the image processor, or another computer, will attempt to align the outer border of the object 26 as seen along the Z-axis and encoded in entity E with optical elements in the 2D color image encoded in entity N. Thereafter, the color value C of each X'-Y' coordinate of entity N is mapped to the appropriate data point of entity E having the aligned X-Y coordinates corresponding thereto. The color mapping operation to create entity I may be executed by any suitable microprocessor means, typically processor 24 of the device 100 (FIG. 4B).

The main optics 41, main illumination source 31, detection optics 60 and image processor 24 are now described with reference to FIGS. 4A and 4B which illustrate, by way of a block diagram an embodiment of a system 20 for confocal imaging of a three dimensional structure according to WO 00/08415 assigned to the present assignee, the contents of which are incorporated herein. Alternatively, any suitable confocal imaging arrangement may be used in the present device.

The system 20 comprises an optical device 22 coupled to a processor 24. Optical device 22 comprises, in this specific embodiment, a semiconductor laser unit 28 emitting a laser light, as represented by arrow 30. The light passes through a polarizer 32 which gives rise to a certain polarization of the light passing through polarizer 32. The light then enters into an optic expander 34 which improves the numerical aperture of the light beam 30. The light beam 30 then passes through a module 38, which may, for example, be a grating or a micro lens array which splits the parent beam 30 into a plurality of incident light beams 36, represented here, for ease of illustration, by a single line. The operation principles of module 38 are known per se and the art and these principles will thus not be elaborated herein.

The optical device 22 further comprises a partially transparent mirror 40 having a small central aperture. It allows transfer of light from the laser source through the downstream optics, but reflects light traveling in the opposite direction. It should be noted that in principle, rather than a partially transparent mirror other optical components with a similar function may also be used, e.g. a beam splitter. The aperture in the mirror 40 improves the measurement accuracy of the apparatus. As a result of this mirror structure the light beams will yield a light annulus on the illuminated area of the imaged object as long as the area is not in focus; and the annulus will turn into a completely illuminated spot once in focus. This will ensure that a difference between the measured intensity when out-of- and in-focus will be larger. Another advantage of a mirror of this kind, as opposed to a beam splitter, is that in the case of the mirror internal reflections which occur in a beam splitter are avoided, and hence the signal-to-noise ratio improves.

The unit further comprises a confocal optics 42, typically operating in a telecentric mode, a relay optics 44, and an endoscopic probing member 46. Elements 42, 44 and 46 are generally as known per se. It should however be noted that telecentric confocal optics avoids distance-introduced magnification changes and maintains the same magnification of the image over a wide range of distances in the Z direction (the Z direction being the direction of beam propagation). The relay optics enables to maintain a certain numerical aperture of the beam's propagation.

The endoscopic probing member 46 typically comprises a rigid, light-transmitting medium, which may be a hollow object defining within it a light transmission path or an object made of a light transmitting material, e.g. a glass body or tube. At its end, the endoscopic probe typically comprises a mirror of the kind ensuring a total internal reflection and which thus directs the incident light beams towards the teeth segment 26. The endoscope 46 thus emits a plurality of incident light beams 48 impinging on to the surface of the teeth section.

Incident light beams 48 form an array of light beams arranged in an X-Y plane, in the Cartesian frame 50, propagating along the Z axis. As the surface on which the incident light beams hits is an uneven surface, the illuminated spots 52 are displaced from one another along the Z axis, at different $(X_i, Y_i)$ locations. Thus, while a spot at one location may be in focus of the optical element 42, spots at other locations may be out-of-focus. Therefore, the light intensity of the returned light beams (see below) of the focused spots will be at its peak, while the light intensity at other spots will be off peak. Thus, for each illuminated spot, a plurality of measurements of light intensity are made at different positions along the Z-axis and for each of such $(X_i, Y_i)$ location, typically the derivative of the intensity over distance (Z) will be made, the $Z_i$ yielding maximum derivative, $Z_0$, will be the in-focus distance. As pointed out above, where, as a result of use of the punctured mirror 40, the incident light forms a light disk on the surface when out of focus and a complete light spot only when in focus, the distance derivative will be larger when approaching in-focus position thus increasing accuracy of the measurement.

The light scattered from each of the light spots includes a beam traveling initially in the Z-axis along the opposite direction of the optical path traveled by the incident light beams. Each returned light beam 54 corresponds to one of the incident light beams 36. Given the unsymmetrical properties of mirror 40, the returned light beams are reflected in the direction of the detection optics 60. The detection optics 60 comprises a polarizer 62 that has a plane of preferred polarization oriented normal to the plane polarization of polarizer 32. The returned polarized light beam 54 pass through an imaging optic 64, typically a lens or a plurality of lenses, and then through a matrix 66 comprising an array of pinholes. CCD camera has a matrix or sensing elements each representing a pixel of the image and each one corresponding to one pinhole in the array 66.

The CCD camera is connected to the image-capturing module 80 of processor unit 24. Thus, each light intensity measured in each of the sensing elements of the CCD camera is then grabbed and analyzed, in a manner to be described below, by processor 24.

Unit 22 further comprises a control module 70 connected to a controlling operation of both semi-conducting laser 28 and a motor 72. Motor 72 is linked to telecentric confocal optics 42 for changing the relative location of the focal plane of the optics 42 along the Z-axis. In a single sequence of operation, control unit 70 induces motor 72 to displace the optical element 42 to change the focal plane location and then, after receipt of a feedback that the location has changed, control module 70 will induce laser 28 to generate a light pulse. At the same time, it will synchronize image-capturing module 80 to grab data representative of the light intensity from each of the sensing elements. Then in subsequent sequences the focal plane will change in the same manner and the data capturing will continue over a wide focal range of optics 44.

Image capturing module 80 is connected to a CPU 82, which then determines the relative intensity in each pixel over the entire range of focal planes of optics 42, 44. As explained above, once a certain light spot is in focus, the measured intensity will be maximal. Thus, by determining the $Z_i$ corresponding to the maximal light intensity or by determining the maximum displacement derivative of the light intensity, for each pixel, the relative position of each light spot along the Z-axis can be determined. Thus, data representative of the three-dimensional pattern of a surface in the teeth segment, can be obtained. This three-dimensional representation may be displayed on a display 84 and manipulated for viewing, e.g. viewing from different angles, zooming-in or out, by the user control module 86 (typically a computer keyboard).

The device 100 further comprises means for providing a 2D color image of the same object 26, and any suitable technique may be used for providing the color image. A number of such techniques are described below.

Figure 4A:
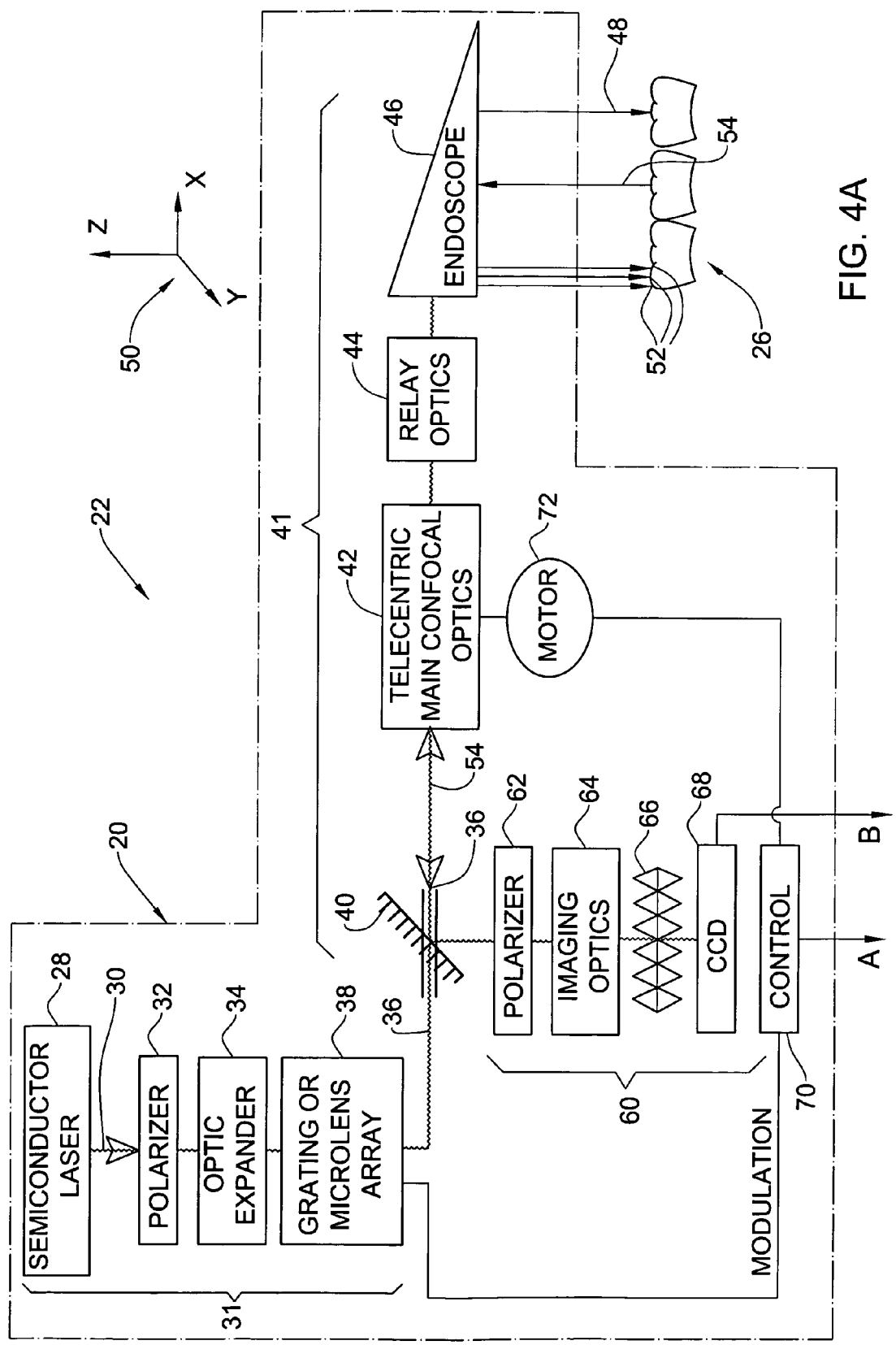
FIGS. 4A and 4B schematically illustrate the main elements of a portion of a device used for providing a three dimensional monochrome entity.
Figure 4B:
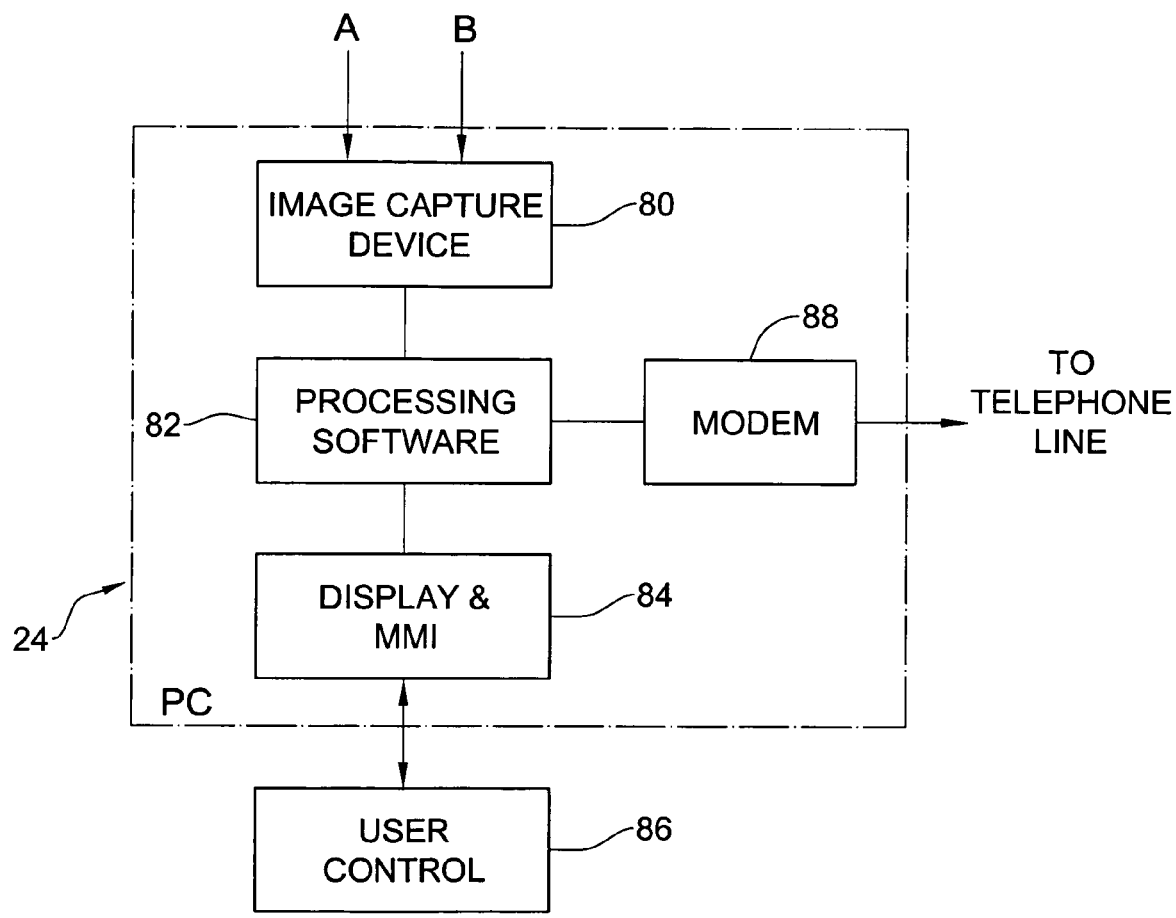

The first technique is based on illuminating the object 26 sequentially with three different colored lights such as red, green and blue, and capturing a monochromatic image corresponding to each color via CCD 68 and the image capture device 80 (see FIGS. 4A, 4B). Referring to FIG. 1, tri-color light sources 71, i.e., one or more light sources that provide illuminating radiations to the object 26 in a plurality of different colors, are coupled to a tri-color sequence generator 74, which are suitably controlled by the processing unit 24 to provide the three colored illuminations via delivery optics 73 in a predetermined sequence. The colored illuminations are provided at a relative short time interval, typically in the range of about 0 to 100 milliseconds, I some cases being in the order of 50 milliseconds, with respect to the 3D scan, directly before or after the same. Suitable processing software 82 combines the three images to provide a 2D color image comprising an array of data points having location (X,Y) and color (C) information for each pixel of the 2D color image.

Figure 5A:
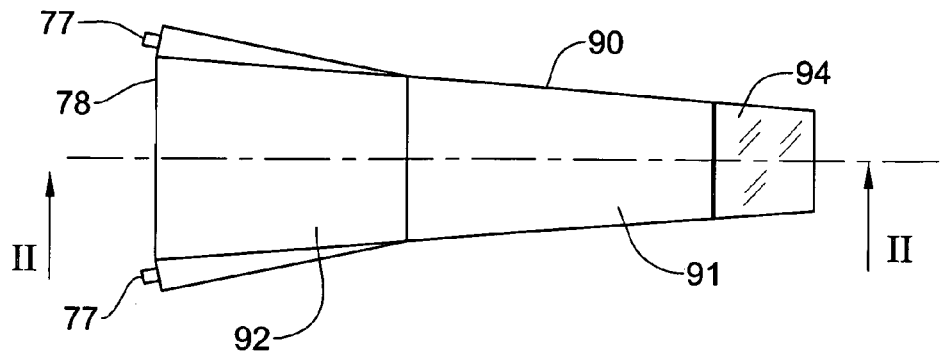
FIGS. 5A, 5B, 5C illustrate in plan view, side view and isometric view, respectively, a probe used in first embodiment of the device of FIG. 1 to provide a two dimensional color entity.
Figure 5B:
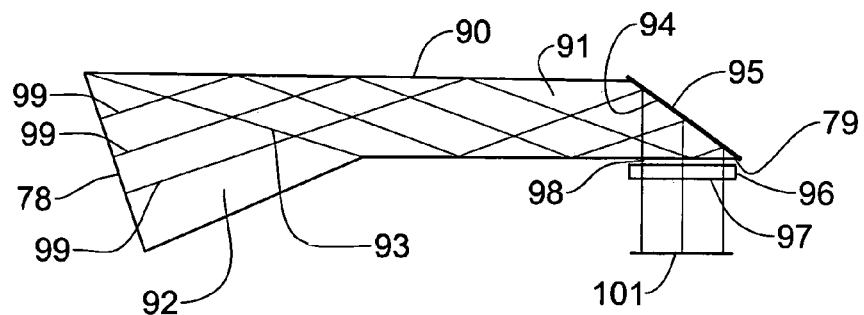
Figure 5C:
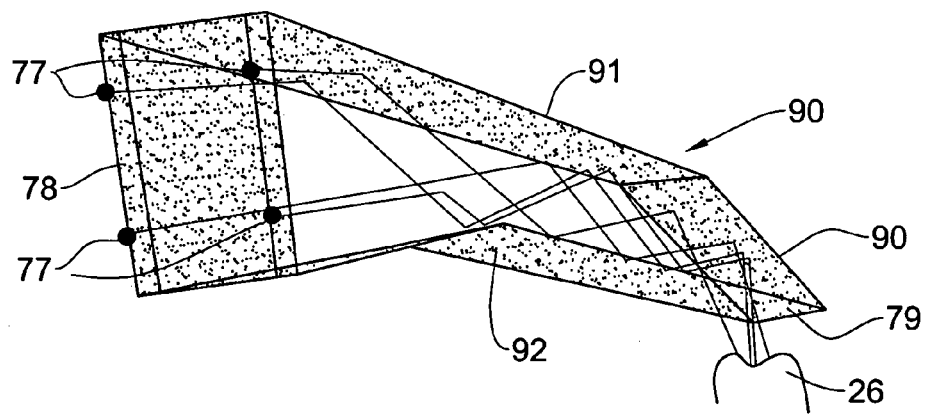

According to a first embodiment of the device 100, the delivery optics 73 is integral with endoscope 46, which is in the form of a probing member 90, as illustrated in FIGS. 5A, 5B and 5C. The probing member 90 is made of a light transmissive material, typically glass and is composed of an anterior segment 91 and a posterior segment 92, tightly glued together in an optically transmissive manner at 93. Slanted face 94 is covered by a totally reflective mirror layer 95. Glass disk 96 defining a sensing surface 97 may be disposed at the bottom in a manner leaving an air gap 98. The disk is fixed in position by a holding structure which is not shown. Three light rays are 99 from the main optics 42 are represented schematically. As can be seen, they bounce at the walls of the probing member at an angle in which the walls are totally reflective and finally bounce on mirror 95 and reflected from there out through the sensing face 97. The light rays focus on focusing plane 101, the position of which can be changed by the focusing optics (not shown in this figure). The probe member 90 comprises an interface 78 via which optical communication is established with the relay optics 44 and the remainder of the device 100. The probe 90 further comprises a plurality of tri-color LED's 77, for providing the colored illumination to the object 26.

The LED's 77 typically comprise different LED's for providing blue radiation and green radiation when red illuminating radiation is used as the illumination source 31 for the main optics 41 when creating the 3D entity. Alternatively, if a blue illuminating radiation is used as the illumination source 31, the LED's 77 may comprise green and red LED's, and if a green illuminating radiation is used as the illumination source 31, LED's 77 may comprise blue and red LED's.

The tri-color LED's 77 are each capable of providing an illumination radiation in one of three colors, typically red, green or blue, as controlled via the tri-color sequence generator. Alternatively, a plurality of LED's in three groups, each group providing illumination in one of the desired colors, may be provided. The LED's 77 are located at the periphery of the interface 78 such that the LED's do not interfere with the other optical operations of the device 100. In particular such operations include the transmission of the illuminating radiation for the confocal focusing operations, and also the transmission of reflected light from the object 26 to the main optics 41 to provide the 3D entity or the 2D color entity. The LED's are mounted substantially orthogonally with respect to the interface 78, and thus, as illustrated in FIG. 5C, light from each of the LED's 77 is transmitted by internal reflection with respect to the walls of the probe 90, to the user interface end 79 of the probe.

Preferably, the device 100 according to a variation of the first embodiment is further adapted for providing improved precision of the color data obtained therewith, in a similar manner to that described herein for the fourth embodiment, mutatis mutandis.

Figure 6:
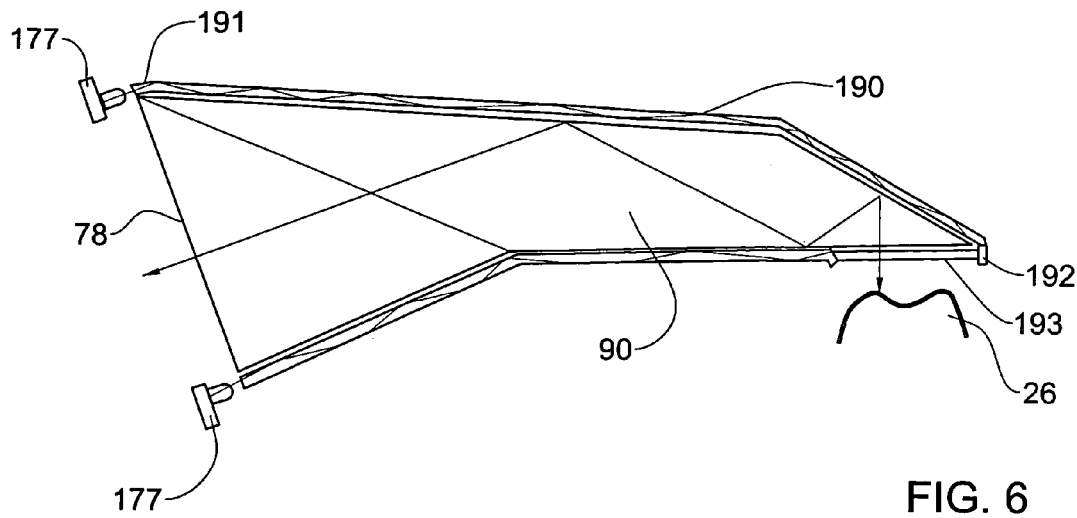
FIG. 6 illustrates in side view a sheath for a probe used in second embodiment of the device of FIG. 1 to provide a two dimensional color entity.

According to a second embodiment of the device 100, the endoscope 46, is also in the form of a probing member 90, substantially as described with respect to the first embodiment, but with the difference that there are no LED's directly mounted thereon at the interface 78, mutatis mutandis. In the second embodiment the delivery optics 73 is in the form of a disposable sleeve, shroud or sheath 190 that covers the outer surface the probing member 90, as illustrated in FIG. 6. The sheath 190 is made from a waveguiding material, such as an acrylic polymer for example, capable of transmitting an illuminating radiation from the upstream face 191 of the sheath 190 therethrough and to the downstream face 192 thereto. The upstream face 191 is in the form of a peripheral surface around the interface 78. The downstream face 192 is formed as a peripheral projection surrounding a window 193 comprised in said sheath 190. The window 193 is in registry with the user interface end 79 of the probe 90. A plurality of tri-color LED's 177 for providing the colored illumination to the object 26 are mounted on the device 100 just upstream of the sheath 190. The tri-color LED's 177 are each capable of providing an illumination radiation in one of three colors, typically red, green or blue, as controlled via the tri-color sequence generator 74. Alternatively, a plurality of LED's in three groups, each group providing one colored illumination, may be provided. The LED's 177 are located outside of the main optics of the device 100, and thus the LED's do not interfere with the other optical operations of the device 100 in particular including the transmission of the illuminating radiation for the confocal focusing operations, or in the transmission of reflected light from the object 26 to provide the 3D entity or the 2D color entity. The LED's are mounted substantially opposite to the upstream face 191, and thus, as illustrated in FIG. 6, light from each of the LED's 177 is transmitted by the waveguiding sheath 190 to downstream face 192 and thence to the object 26. In this embodiment, the sheath 190 is particularly useful in maintaining hygienic conditions between one patient and the next, and avoids the need for sterilizing the probe 90, since the sheath may be discarded after being used with one patient, and replaced with another sterilised sheath before conducting an intra-oral cavity survey with the next patient.

Preferably, the device 100 according to a variation of the second embodiment is further adapted for providing improved precision of the color data obtained therewith, in a similar manner to that described herein for the fourth embodiment, mutatis mutandis.

In either one of the first or second embodiments, or variations thereof, a red laser may be used as the illumination source 28 for the main optics when creating the 3D entity. As such, this illumination means may also be used to obtain the red monochromatic image for the creation of the 2D color image, by illuminating the object 26 and recording the image with the optical detector 60. Accordingly, rather than tri-color LED's or LED's or three different colors, it is only necessary to provide LED's adapted to provide only the remaining two colors, green and blue. A similar situation arises if the illumination source for the main optics 41 is a green or blue laser, wherein illuminating radiations in only the remaining two colors need to be provided, mutatis mutandis.

In these embodiments, the positioning of the illumination sources at the upstream end of the probe 90 where there is ample room rather than at the patient interface end 79 where space is tight.

Figure 7A:
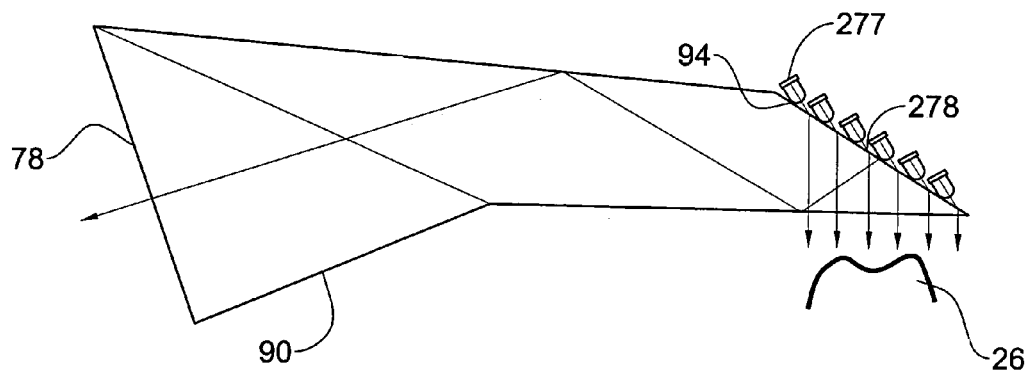
FIG. 7A illustrates in side view a probe used in third embodiment of the device of FIG. 1 to provide a two dimensional color entity.
Figure 7B:
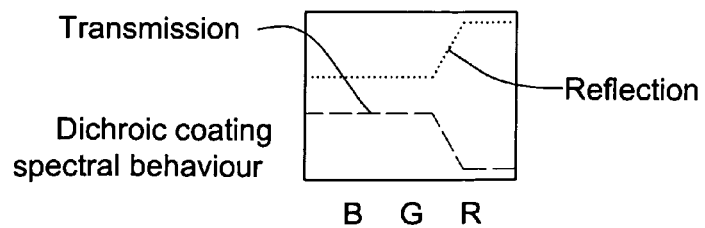
FIG. 7B illustrates the transmission and reflection characteristics of a typical dichroic coating used in the probe of FIG. 7A.

According to a third embodiment of the device 100, the endoscope 46 is also in the form of a probing member 90, substantially as described with respect to the second embodiment with the following differences, mutatis mutandis. As illustrated in FIG. 7A, in the third embodiment the delivery optics 73 comprises a plurality of LED's 277 for providing the colored illumination to the object 26. In this embodiment, a red laser is used as the illumination source for the main optics when creating the 3D entity. As such, this illumination means is also used to obtain the red monochromatic image for the creation of the 2D color image. Thus, the LED's 277 are each capable of providing an illumination radiation in either green or blue, as controlled via the tri-color sequence generator 74. The LED's 277 are located on the outer side of slanted face 94, and thus the LED's do not interfere with the other optical operations of the device 100 in particular including the transmission of the illuminating radiation for the confocal focusing operations, or in the transmission of reflected light from the object 26 to provide the 3D entity or the 2D color entity. The slanted face 94 comprises a dichroic coating 278 on the outer side thereof, which has relatively high reflectivity and low transmission properties with respect to red light, while having substantially high transmission characteristics for blue light and green light, as illustrated in FIG. 7B. Thus, as illustrated in FIG. 7A, light from each of the blue or green LED's 277 is transmitted, in turn, through the dichroic coating to interface 79 and thence to the object 26, as controlled by the generator 74. At the same time the dichroic coating permits internal reflection of the red radiation from the main optics 41 to the interface 79 and object 26, and thus allows the 3D scan to be completed, as well as allowing the red monochromatic image of the object 26 to be taken by the device 100. Optionally, rather than employing blue and green LED's, tricolor LED's may be used, and properly synchronized to illuminate with either green or blue light as controlled by generator 74. Alternatively, the illumination source for the main optics 41 may be a green or blue laser, in which case the LED's are each capable of providing illumination in the remaining two colors, and in such cases the dichroic coating is adapted for allowing transmission of these remaining two colors while providing substantially high reflection for the illuminating laser of the main optics, in a similar manner to that described above for the red laser, mutatis mutandis.

Figure 8:
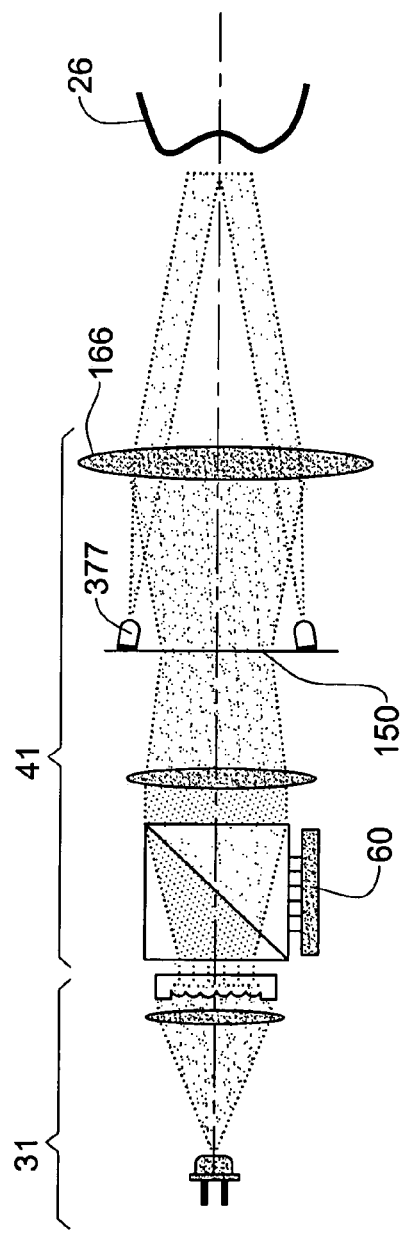
FIG. 8 illustrates in side view the general arrangement of the main elements used in fourth embodiment of the device of FIG. 1 to provide a two dimensional color entity.

In a fourth embodiment of the device 100, and referring to FIG. 8, tri-color illumination is provided within the main focal optics 42, in particular at the confocal system aperture stop, and facing the objective lens of the system. An advantage provided by this form of illumination is that the tri-color illumination illuminates the object 26 through the downstream objective lens 142 in nearly collimated light, and thus the object illumination is highly uniform. The tri-color light sources 377 may be mounted statically on the physical aperture stop at the aperture stop plane 150, or alternatively they may be mounted on a retracting aperture stop, which also serves to stop down the system aperture in preview mode. In this embodiment, by placing the tri-color light sources 377 at the aperture stop plane, wherein the light beam from the illumination source 31 narrows to a minimum within the main optics 41, the external dimensions of the device 100 may still remain relatively compact.

Figure 9:
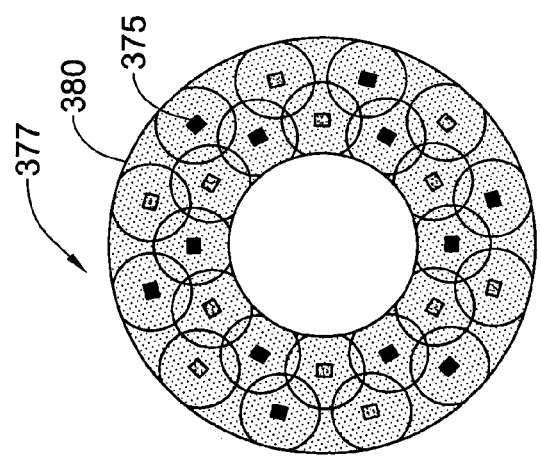
FIG. 9 illustrates an LED arrangement used with the embodiment of FIG. 8.

Referring to FIG. 9, the tri-color light sources 377 may comprise, for example, a plurality of tri-color LED's 385 mounted onto a bracket 380. The bracket 380 is typically annular, having a central aperture to allow illumination light from the illuminating unit 31 to pass therethrough and to the object 26, and to allow light coming from the object 26 to pass therethrough and to the detection optics 60, without being affected by the bracket 380. At the same time, the bracket 380 positions the LED's in the required location upstream of objective lens 166. The LED's are arranged in a spaced radial and circumferential manner as illustrated in FIG. 9 to provide the most uniform illumination of the object 26 possible with this arrangement. Typically, a red laser is used as the illumination source 31 for the main optics 41 when creating the 3D entity. As such, and as in other embodiments, this illumination means is also used to obtain the red monochromatic image for the creation of the 2D color image. Thus, the LED's 385 are each capable of providing an illumination radiation in either green or blue, as controlled via the tri-color sequence generator 74. Alternatively, the illumination source for the main optics 41 may be a green or blue laser, in which case the LED's 385 are each capable of providing illumination in the remaining two colors, in a similar manner to that described above for the red laser, mutatis mutandis. Optionally, rather than employing blue and green LED's, tricolor LED's may be used, and properly synchronized to illuminate with either green or blue light as controlled by generator 74. Further optionally, the LED's 385 may be used to provide, sequentially, all the required colored illuminations, typically red, green and blue. Alternatively, the LED's 385 each provide illumination in one of at least three colors. Thus, some of the LED's 385 provide a blue illumination, while other LED's 385 provide green illumination, while yet other LED's 385 provide red illumination.

Preferably, the device 100 according to a variation of the fourth embodiment is further adapted for providing improved precision of the color data obtained therewith. In this connection, the device 100 according to this variation of the fourth embodiment is adapted such that the tri-color light sources 377 each illuminate the object 26 with as wide a depth of field as possible, i.e., at a low numerical aperture. Thus, each set of light sources 377 of the same color, for example blue, illuminates a particular depth of the object 26 in the z-direction while substantially in focus. In contrast, the numerical aperture of the confocal system itself is relatively high to maximize accuracy of the depth measurements, and thus provides a relatively narrower depth of field.

Advantageously, the optical system downstream of the light sources 377, in this embodiment the objective lens 166, is chromatic, and in particular maximizes the chromatic dispersion therethrough. Alternatively or additionally, a chromatic dispersion element, for example an optically refractive block of suitable refractive index, may be provided along the optical path between the light sources 377 and the object 26. Thus, each one of the different-colored light sources 377 illuminates a different portion of the object 26 along the z-direction. The light sources 377 providing the blue illumination illuminate in focus a portion of the object 26 closest to the device 100, and the light sources 377 providing the red illumination illuminate in focus a portion of the object 26 furthest from the device 100. At the same time, the light sources 377 providing the green illumination illuminate in focus a portion of the object 26 intermediate the blue and red portions, and a non-illuminated gap may exists between the red and green, and between the green and blue illuminated portions, the depth of these gaps depending on the dispersion characteristics of the downstream optics. Advantageously, the light sources 377 are also adapted for providing illumination in colors intermediate in wavelengths such as to illuminate the aforesaid gaps in focus. Thus, the LED's 385 may be adapted for providing both such additional colored illumination, or some of the LED's 385 may be adapted to provide colored illumination at a first intermediate wavelength, while another set of LED's 385 may be adapted to provide colored illumination at a second intermediate wavelength. For example, the first intermediate wavelength provides an illumination in aqua, and thus illuminates in focus at least a part of the gaps between the blue and green illuminated focused zones of the object 26, while the second intermediate wavelength provides an illumination in amber, and thus illuminates in focus at least a part the gaps between the green and red illuminated focused zones. Of course, additional light sources may be used to provide further intermediate wavelengths and thus provide further depth cover illumination, in focus, of the object.

While the device 100 is used as a viewfinder, typically prior to taking a depth and color scan of the object 26, the above arrangement using at least five different colored illuminations at a low numerical aperture, enables a much clearer and focused real-time color image of the object 26 to be obtained. Thus when in operation in viewfinder mode (also known as "aiming mode", prior to the 3D scan event, while the dental practitioner is in the process of aiming the scanner onto the target dental surface, for example) the device 100 according to this variation of the fourth embodiment repeatedly illuminates the object 26 in cycles, wherein in each cycle the object 26 is separately illuminated in each of the five colors blue, aqua, green, amber, red, in quick succession, and each time a monochromatic image is obtained by the monochromatic image sensor in 60. Each set of five monochromatic images is then analysed to provide a composite color image, and this image is then displayed in substantially real time in the viewfinder display window in the control software, so that the succession of such composite images gives the appearance of a substantially real-time color video feed of the object 26.

Each of the monochrome images in any particular set corresponds to a particular illumination color or wavelength, and thus the zone(s) of the object 26 within the depth of field corresponding to this illumination will be in focus, while the other parts of the object 26 will appear out of focus. Thus, each such image in the aforesaid set of images will contain a portion which has high precision focused image of a part of the object, for the particular illumination wavelength.

In forming a composite image for each set of images, the images are combined in such a way as to maximize the precision of the focused image and corresponding color thereof. Thus, for example, suitable algorithms may be applied to each of the five images of a set to distinguish between the focused and unfocused the areas thereof. Such algorithms may employ, for example, techniques which apply FFT techniques to areas of the images, and which search for high frequency portions which correspond to focused areas. In any case, such algorithms, as well as software and hardware to accomplish the same are well known in the art. Then, the focused areas of each of the five images are merged to provide a monochrome composite substantially focused image of the object. Next, the images obtained using the red, green and blue illuminations are combined and converted to a corresponding luminescence/chroma (Y/C) image, and techniques for doing so are well known in the art. Finally, the luminescence component of the luminescence/chroma (Y/C) image is replaced with the aforesaid corresponding composite focus image, and the resulting new luminescence/chroma image is then transmitted to the display in the viewfinder.

For each set of images, prior to combining the corresponding red, green and blue images, these are preferably first scaled to compensate for magnification effects of the different wavelengths. Thus, the green image, and more so the blue image, needs to be scaled up to match the red image.

When the user is ready to take a depth and color scan of the object 26, having steered the device 100 into position with the aid of the viewfinder, the device 100 takes a depth scan in the z-direction as described herein, and either before or after the same, but in quick succession one with the other, takes a color scan in a similar manner to that described above for the viewfinder mode, mutatis mutandis. Subsequently, the color data and the depth data of the two scans can be combined to provide the full spatial and color data for the surface scanned.

Advantageously, one or more color scans may also be taken during the depth scan, and/or at the beginning and at the end of the depth scan. In one mode of operation, the depth scan is obtained by displacing the objective lends 166 along the z-direction in a continuous or stepped motion. Multiple color scans can then be obtained by associating the color sources 377 with the objective lens, so that these are also displaced along the z-direction. Accordingly, as the light sources 377 are moved in the z-direction towards the object 26 during the depth scan, at each different z-position in which a set of images is taken (concurrently with or alternately with the depth scan), each one of the colored illuminations—red, green, blue and intermediate wavelengths—illuminates a progressively deeper part of the object along the z-direction. Of course, in some cases it is possible that at the downstream end of the depth scan the green and red illuminations completely overshoot the object 26, and the corresponding images may be discarded or otherwise manipulated to provide a composite color image at this station. Thus, a plurality of color images can be obtained, each based on a different z-position, so that each illumination wavelength is used to illuminate in focus a different part (depth) of the object 26. Advantageously, suitable algorithms may be used to form a composite color image of the set of color images associated with a particular z-scan of the object 26 to provide even more precise and accurate color image, than can then be combined with the depth data.

Alternatively, and referring to FIG. 10, the tri-color light sources 377 may be replaced with a rotating filter illumination system 400. The system 400 comprises a while light source 410, such as for example white phosphorus InGaN LED's, and the light therefrom is focused onto an optical fiber bundle 420 by means of condenser optics 430. Between the condenser optics 430 and the fiber bundle 420 is provided a rotating tri-color filter 450. As best seen in FIG. 10A, the filter 450 is divided into three colored sections, comprising blue, green and red filters on adjacent sectors therein. The fiber bundle 420 is flared at the downstream end 470 to form the desired illumination pattern. Optionally, the downstream end 470 of the fibers may be mounted onto an annular bracket similar to bracket 380 illustrated in FIG. 9, at the aperture stop plane of the confocal optics. A suitable motor 460, typically a stepper motor for example, drives the rotating filter such as to sequentially present each colored filter to the light passing from the condenser optics 430 to the fiber bundle 420, as synchronized with the sequence generator 74 (FIG. 1) to enable the detection optics 60 to capture images of the object 26 when selectively illuminated with each of the three colors. Optionally, if a red, blue or green illuminating radiation is used as the illumination source 31 for the main optics 41 when creating the 3D entity, then the rotating filter 450 only requires to comprise the remaining two colors, as discussed above for similar situations regarding the LED's, mutatis mutandis.

Preferably, the device 100 according to this variation of the fourth embodiment may be further adapted for providing improved precision of the color data obtained therewith, in a similar manner to that described herein for another variation of fourth embodiment, mutatis mutandis. In particular, the filter 450 is divided into five (or more if desired) colored sections, comprising blue, aqua, green, amber and red filters on adjacent sectors therein.

A fifth embodiment of system 100 is substantially similar to the fourth embodiment as described herein, with the following difference, mutatis mutandis. In the fifth embodiment, and referring to FIG. 11, polarizer are provided at two locations in order to increase the image contrast. A first polarizing element 161 is located just downstream of the light sources 377 so as to polarize the light emitted from the light sources 377. A second polarizing element 162 is located just upstream of the image sensor of the detection optics 60, and is crossed with respect to the first polarizing element 161. Further, a quarter waveplate 163 is provided just upstream of the object 26, i.e. at the downstream end of the endoscope 46 (FIG. 4A). The first polarizing element 161 is typically annular, having a central aperture to allow illumination light from the illuminating unit 31 to pass therethrough and to the object, and to allow light coming from the object 26 to pass therethrough and to the detection optics 60, without being affected by the polarizing element 161. However, light that is reflected from the object 26 returns to the main confocal optics 42 in a crossed polarization state due to the effect of the quarter waveplate 163, and thus reaches the detection optics 60 at substantially full intensity. However, any light reflected from the objective lens 166 of the confocal optics 42 is reflected at the same polarization state, and is therefore filtered out by the crossed polarizing element 162. This arrangement serves as an effective signal to ghost enhancement system.

Preferably, the device 100 according to a variation of the fifth embodiment is further adapted for providing improved precision of the color data obtained therewith, in a similar manner to that described herein for the fourth embodiment, mutatis mutandis.

Figure 12:
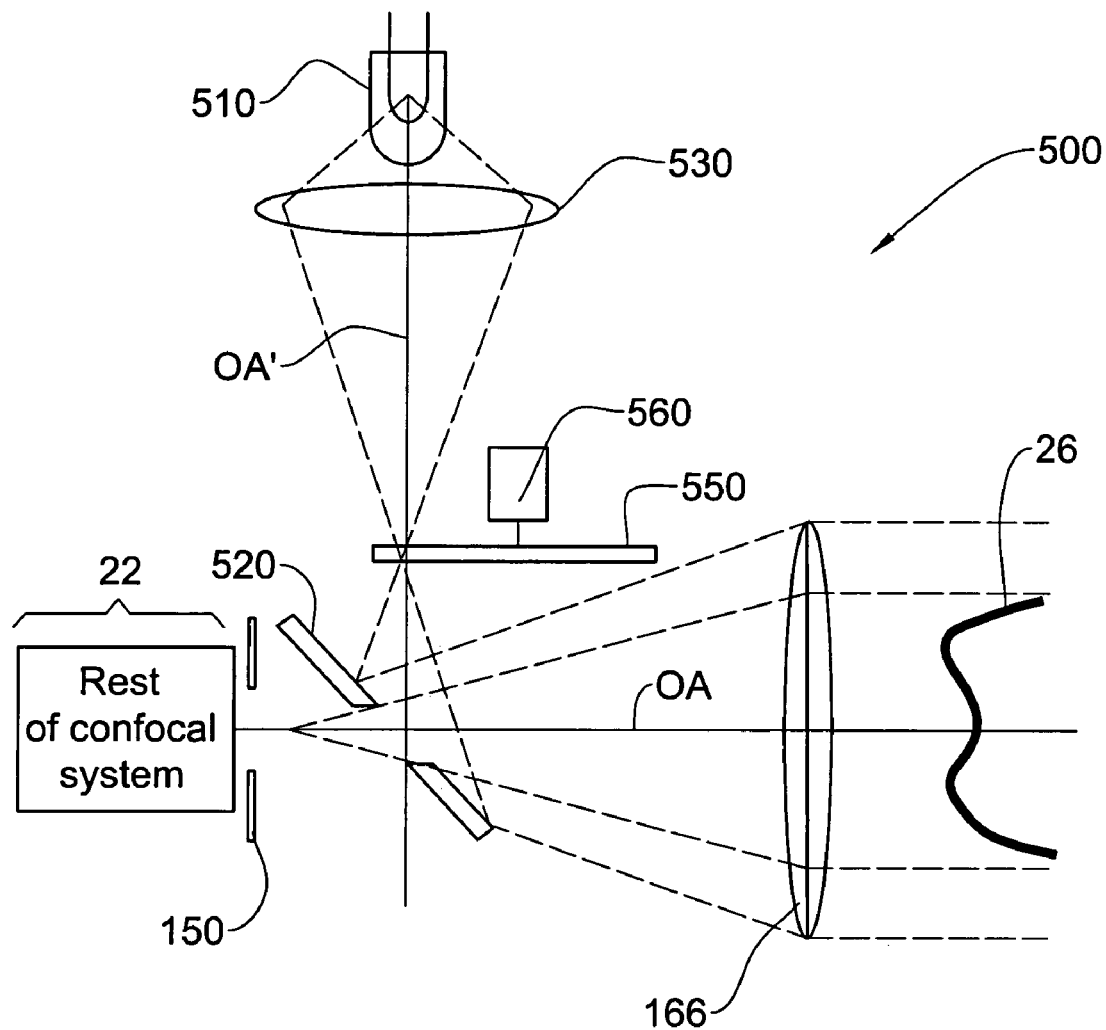
FIG. 12 illustrates in side view the general arrangement of the main elements used in sixth embodiment of the device of FIG. 1 to provide a two dimensional color entity.

A sixth embodiment of the system 100 is substantially as described for the fourth embodiment, with the following difference, mutatis mutandis. In the sixth embodiment, and referring to FIG. 12, the tri-color light sources 377 are replaced with a rotating filter illumination system 500. The system 500 comprises a while light source 510, such as for example white phosphorus InGaN LED's, and the light therefrom is focused onto a mirror 520 by means of condenser optics 530. Between the condenser optics 530 and the mirror 520 is provided a rotating tri-color filter 550, which is similar to the filter 450 illustrated in FIG. 11, and thus comprises three colored sections, comprising blue, green and red filters on adjacent sectors therein, and is actuated by motor 560. The optical axis OA of the confocal optics 41 is orthogonal to the optical axis OA' of the light source 510 and condenser optics 530. The mirror 520 is mounted between the aperture stop plane and the objective lens 166 of the confocal optics, and at an angle to the optical axis OA thereof and to the optical axis OA' of the light source 510 and condenser optics 530. The mirror 520 is typically annular, having a central aperture aligned with optical axis OA to allow illumination light from the illuminating unit 31 to pass therethrough and to the object 26, and to allow light coming from the object 26 to pass therethrough and to the detection optics 60, without being affected by the mirror 520. At the same time, the mirror 520 has sufficient reflecting surface to reflect light from the source 510 via objective lens 166 and to the object 26. Optionally, if a red, blue or green illuminating radiation is used as the illumination source 31 for the main optics 41 when creating the 3D entity, then the rotating filter 550 only requires the remaining two colors, as discussed above for similar situations, mutatis mutandis.

Preferably, the device 100 according to a variation of the sixth embodiment is further adapted for providing improved precision of the color data obtained therewith, in a similar manner to that described herein for the fourth embodiment, mutatis mutandis.

Figure 13:
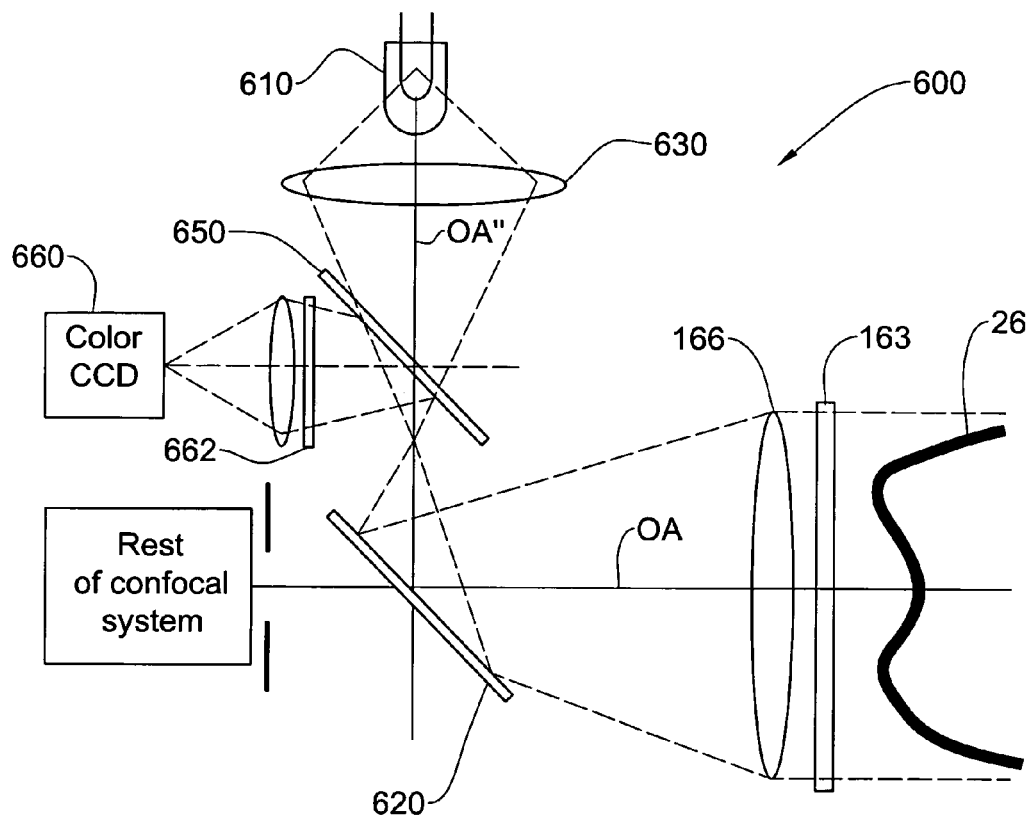
FIG. 13 illustrates in side view the general arrangement of the main elements used in seventh embodiment of the device of FIG. 1 to provide a two dimensional color entity.

According to a second technique for providing the aforesaid 2D color image, the object 26 is illuminated with a white light, and a color CCD is used for receiving the light reflected from the object 26. Thus, a seventh embodiment of the system 100 comprises a white light illumination system 600, illustrated in FIG. 13. The system 600 comprises a while light source 610, such as for example white phosphorus InGaN LED's, and the light therefrom is directed onto a flip mirror 620 via a polarizing beam splitter 650 by means of condenser optics 630. The optical axis OA of the confocal optics 41 is orthogonal to the optical axis OA" of the light source 610 and condenser optics 630. The mirror 620 is mounted between the aperture stop plane 155 and the objective lens 166 of the confocal optics, and at an angle to the optical axis OA thereof and to the optical axis OA" of the light source 610 and condenser optics 630.

The mirror 620 is adapted to flip away from optical axis OA when the device 100 is being used for obtaining the 3D entity E. This allows illumination light from the illuminating unit 31 to pass therethrough and to the object 26, and to allow light coming from the object 26 to pass therethrough and to the detection optics 60, without being affected by the mirror 620. When it is desired to take a 2D color image, the mirror 620 is flipped down to the position shown in FIG. 13. Polarizing beam splitter 650 that polarizes white light from the source 610 and allows the same to pass therethrough and to mirror 620, and thence to the object 26 via the confocal objective 166 and broadband quarter wave plate 163. Light that is reflected from the object 26 returns to the mirror 620 in a crossed polarization state due to the effect of the quarter waveplate 163, and thus reaches the color CCD 660 (and associated detection optics—not shown) at substantially full intensity. However, any light reflected from the objective lens 166 of the confocal optics 42 is reflected at the same polarization state, and is therefore filtered out by a crossed polarizing element 662 just upstream of the CCD 660. This arrangement serves as an effective signal to ghost enhancement system.

Alternatively, the CCD of the detection optics 60 is a color CCD and is also used for the 2D scan. In such a case, flipping mirror 620 is replaced with a fixed mirror having a central aperture similar to mirror 520, having a central aperture, as described for the sixth embodiment, mutatis mutandis.

In the seventh embodiment, the image capture device 80 and processing software 82 (FIG. 4*b*) automatically provide a 2D color image comprising an array of data points having location (X,Y) and color (C) information for each pixel of the image.

According to a third technique for providing the 2D color image, the object is illuminated with a white light, and the light reflected from the object 26 is passed sequentially through one of three different colored filters such as red, green ad blue. Each time a monochromatic image corresponding to each color is captured via CCD 68 and the image capture device 80 (see FIGS. 4A, 4B). Suitable processing software 82 combines the three images to provide a 2D color image comprising an array of data points having location (X,Y) and color (C) information for each pixel of the image.

According to a fourth technique for providing the color image, the main illumination source 31 of device 100 comprises suitable means for providing the three different colored illuminations. In one embodiment, the illumination source 31 comprises three different lasers, each one providing an illumination radiation at a different desired color, red green or blue. In another embodiment, a suitable white light illumination means is provided, coupled to a suitable rotating tri-color filter, similar to the filters described above, mutatis mutandis. In each case, suitable control means are provided, adapted to illuminate the object 26 with each colored radiation in turn, and the 2D colored image is obtained in a similar fashion to that described above, mutatis mutandis. The object is also illuminated with one of the colored illuminations in order to provide the 3D surface topology data.

In each of the embodiments described herein, the illumination radiation that is used for obtaining the 2D color image is injected into the optical axis OA of the confocal optics 42 without affecting the operation thereof or degrading the 3D image capture.

The endoscope 46, the illumination unit 31, the main optics 41, color illumination 71 and tri-color sequence genetrator are preferably included together in a unitary device, typically a hand-held device. The device preferably includes also the detector optics 60, though the latter may be connected to the remainder of the device via a suitable optical link such as a fiber optics cable.

For all embodiments, the data representative of the surface topology and color, i.e., entity I, may be transmitted through an appropriate data port, e.g. a modem 88 (FIG. 4B), through any communication network, e.g. telephone line 90, to a recipient (not shown) e.g. to an off-site CAD/CAM apparatus (not shown).

By capturing, in this manner, an image from two or more angular locations around the structure, e.g. in the case of a teeth segment from the buccal direction, from the lingual direction and optionally from above the teeth, an accurate color three-dimensional representation of the teeth segment may be reconstructed. This may allow a virtual reconstruction of the three-dimensional structure in a computerized environment or a physical reconstruction in a CAD/CAM apparatus.

While the present device has been described in the context of a particular embodiment of an optical scanner that uses confocal focusing techniques for obtaining the 3D entity, the device may comprise any other confocal focusing arrangement, for example as described in WO 00/08415. In fact, any suitable means for providing 3D scanning can be used so long as the 3D scan and the color 2D scan correspond substantially to the same object or portion thereof being scanned, and the same frames of references are maintained. Typically the scans are executed in relatively quick succession, and by the same or different image capturing means such as CCD's that are arranged such that the color 2D image substantially corresponds to the 3D entity. This enables color values at particular x, y coordinates of the 2D color image to be matched to the same x, y coordinates of the 3D image which also have a z coordinate.

While four main embodiments of the present invention are now described hereinbelow, it may be appreciated that the method of the invention may be used for a very wide variety of applications in which intra oral cavity data may be obtained for use in procedures associated with the oral cavity.

Figure 14:
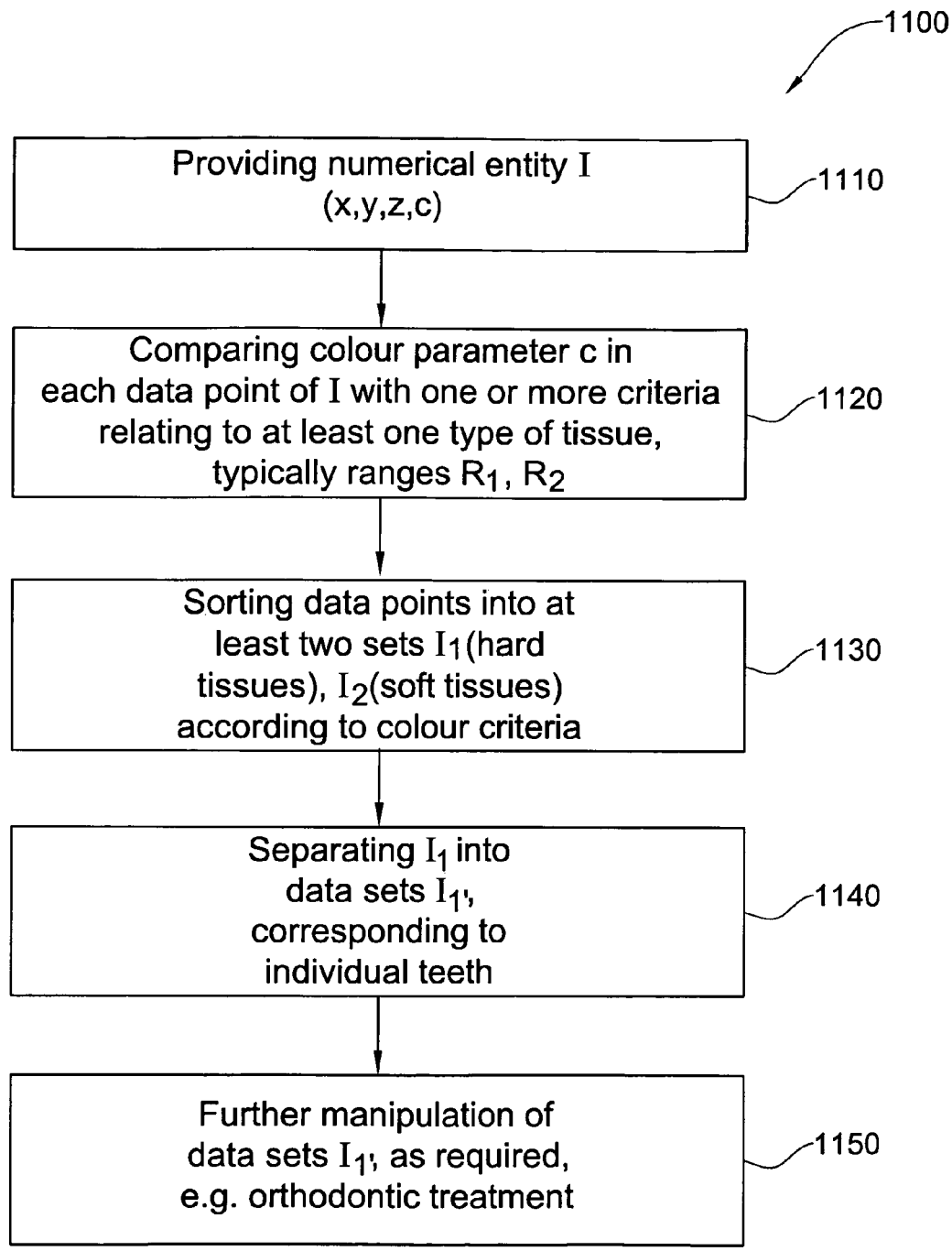
FIG. 14 illustrates the main steps of the method according to the first embodiment of the present invention.

Referring to FIG. 14, in a first embodiment of the present invention, the method of the invention, generally designated 1100, is particularly adapted for automatically differentiating one tissue from another tissue within the oral cavity. As with all embodiments of the invention, the first step 1110 is to obtain numerical entity I comprising a data set representing the surface geometry and color of at least the portion of the intraoral cavity that contains the area of interest, herein referred to as the target surface. The target surface typically comprises both hard tissues, such as the teeth, and soft tissues which include at least one of the gums, tongue, cheeks and lips. Each data point in the numerical entity I comprises surface coordinates of the tissue, typically expressed as Cartesian (x, y, z) coordinates, plus a color parameter relating to the color c of the tissue at these surface coordinates. The color value for c can be conveniently expressed in component form in terms of the red, green and blue components (RGB), and in particular in terms of a color component coefficient. For example, a red coefficient ratio: Rc, may be defined as the intensity of the red component divided by the average intensity of the red, green and blue components, and is useful in differentiating between the hard and soft tissues. The entity I may be obtained, for example, using the device described herein with respect to FIGS. 1 to 13.

In the next step 1120, the value of the color parameter c is analysed for each data point in I, and compared with at least one color criterion, and typically with at least two color ranges $R_1$, $R_2$. The ranges $R_1$, $R_2$ each represent the values of the color parameter expected for one or another of the two tissues, such as the teeth and gums. For example, the color range $R_1$ for the teeth will include values for c typically associated with the hard tissues including the teeth, comprising all appropriate shades appropriate for enamel, dentine, pulp and other parts of teeth. Similarly, the color range $R_2$ for the soft tissues will include values for c typically associated with gums, cheeks, lips and the tongue including all appropriate shades of pink and red associated with these tissues, including when the tissues are at least partially drained of blood, as may happen, for example when the tissues are anaesthetised. In some cases it may be appropriate to compare the value of the color parameter c with a specific value, for example a single (R, G, B) or Rc value, rather than a range of values.

Table I lists typical RGB values measured for gums, lips and teeth of a particular patient. As may be seen from Table I, values of Rc significantly greater than unity indicate that the red component is dominant, which is the case for soft tissues in general. Hard tissues, on the other hand, have a more even distribution of color components, resulting in an Rc value very close to unity.

TABLE I

Intraoral RGB Values measured for a Patient

| Tissue | Red component | Green component | Blue component | Rc = 3 * R/(R + G + B) |
|---|---|---|---|---|
| Gum 1 | 76 | 28 | 28 | 1.6 |
| Gum 2 | 119 | 79 | 80 | 1.28 |
| Lower lip | 165 | 120 | 130 | 1.2 |
| Premolar | 168 | 175 | 167 | 0.99 |
| Incisor | 172 | 174 | 170 | 1.0 |

Thus, an exemplary range for $R_1$ may be from about 0.9 to about 1.1, while an exemplary range for $R_2$ may be from less than about 1.2 to a maximum of 3.0.

The ranges $R_1$, $R_2$ should preferably be sufficiently spaced one from the other and not overlap to facilitate distinction between the different tissues and to prevent ambiguity. At the same time, each range should include all possible variations of color that may be expected for each of the tissues involved.

The actual values of the ranges $R_1$, $R_2$ may vary between individuals. For example, some individuals may have yellowing teeth and pale soft tissues, while others may have milky white teeth and reddish complexion. Optionally, it is possible to pre-calibrate the ranges $R_1$, $R_2$, for example by scanning an area that is purely soft tissue, and another dental area that is purely hard tissue, and using the color values for the two scans as datum values for the two ranges $R_1$, $R_2$.

Optionally, each tissue type may also be associated with more than one range of color values, and thus each one of $R_1$, $R_2$ may comprise a set of ranges. For example, $R_2$ may actually include four separate ranges, each relating to the color variations of one of the gums, cheeks, lips and tongue. Also, $R_1$ may include a number of separate ranges, one range representative of the variations in the color of natural teeth, while the other ranges relate to colors associated with prostheses and/or with fillings, particularly when made from materials which do not give a natural appearance to the prostheses, for example gold crowns or amalgam fillings.

In the next step 1130, the data points for entity I are sorted into at least two sub-data sets, $I_1$, $I_2$, according to the color criteria, that is, for example, whether the value of the color parameter of each data point is within $R_1$ or $R_2$, respectively. Thus, $I_1$ will contain all data points in which the color parameter thereof corresponds to the color of teeth, and thus should comprise the coordinates relating to the surfaces of teeth only within the original entity I (optionally including prostheses and fillings). Similarly, $I_2$ should contain all data points in which the color parameter thereof corresponds to the color of the soft tissues, and thus should comprise the coordinates relating to the soft tissues only within the original entity I.

In a modification to this embodiment, it may only be necessary or desired to identify one tissue, such as the teeth for example, and disregard all data not relating to this tissue. In such cases, it is only necessary to compare the value of the color component of each data point to a single color criterion, such as for example a predetermined range $R_1$ relating to the teeth only, and then separate out these data points from the entity I to provide an entity $I_1$ that comprises data relating only to the teeth. Of course, it may also be desired to include in this data set artificial teeth and also fillings that do not have a natural color, and thus the range $R_1$ may optionally include the appropriate values for the color parameter relating thereto.

Once the original entity I has been separated into two entities, or wherein an entity $I_1$ has been created from the original entity I comprising only the tissue of interest, the new entity may be further manipulated as desired. In step 1140, for example, when the new entity $I_1$ comprises only teeth-related data, each individual tooth may be identified therein. In such a situation, the entity $I_1$ is further separated out into a plurality of smaller entities $I_{1'}$, each of which relates to a separate tooth. Typically, the separation of $I_1$ into $I_{1'}$ is automatically effected using any suitable algorithm In step 1150, after the data relating to the individual teeth has been properly sorted, further manipulation may be carried out for each of the individual data sets of the entities I1', for example to simulate a particular orthodontic treatment for the teeth.

This embodiment may also be applied to the identification of a finish line profile for a crown or bridge prosthesis.

The finish line may be regarded as the circumferential junction or shoulder between the upper prepared portion of the tooth and the lower unprepared portion of the tooth. The finish line may be above or below the visible gum line, i.e. the exterior visible line of gingival tissue which circumferentially surrounds the tooth. Frequently, the finish line is below the visible gum line and is uneven, i.e. the finish line varies in height along the circumferential direction and can rise or fall on the order of several millimeters in the generally vertical direction. The finish line may even, in some cases, extend as far downwardly as the attachment line, i.e. the circumferential line defined by the neck of the tooth and its immediately adjacent gingival tissue below the aforementioned visible gum line. As with the finish line, the attachment line is uneven and also typically varies several millimeters in height along the circumferential direction. The contour of the attachment line varies from tooth to tooth, as well as from patient to patient, and is not readily visible or accessible to the dentist because it is below the visible gum line. In such cases, a retention ring or wire, made of an elastically deformable material, may be placed around the preparation to retract the gum tissue around the preparation. The ring thus in many cases exposes at least part of the emerging profile—the surface of the tooth between the finish line and the gum.

The ring thus adopts a profile which may often be substantially similar to that of the finish line. By having the ring colored sufficiently differently to the color of the teeth or soft tissues, say in blue, it is relatively straightforward to separate out from the entity I all data points having a color component with a value in a specific range corresponding to the color of the ring. Identification of the ring itself provides a useful starting point for suitable algorithms that are then applied to determine the location and geometry of the finish line. Such algorithms are known and typically attempt to identify features commonly found with finish lines such as for example, a discontinuity in the slope of the tooth surface, or a mound-shaped projection corresponding to the preparation. Moreover, separation of the hard tissue from the soft tissue results in a smaller data base that needs to be analysed to identify the finish line. In particular, when the data set has been separated into entities $I_1$, then only the specific entity $I_1$ corresponding to the ring needs to the analysed for the finish line, as this entity corresponds to the preparation.

In all variations of this embodiment, the comparison of value for the color parameter c with an appropriate range, and the sorting of data points into one or more data sets according to this comparison can be executed with any suitable computer with the aid of a suitably constructed program. The manipulation of the entities at each stage with respect to the computer may be manual, interactive, or partially or fully automated.

Figure 15:
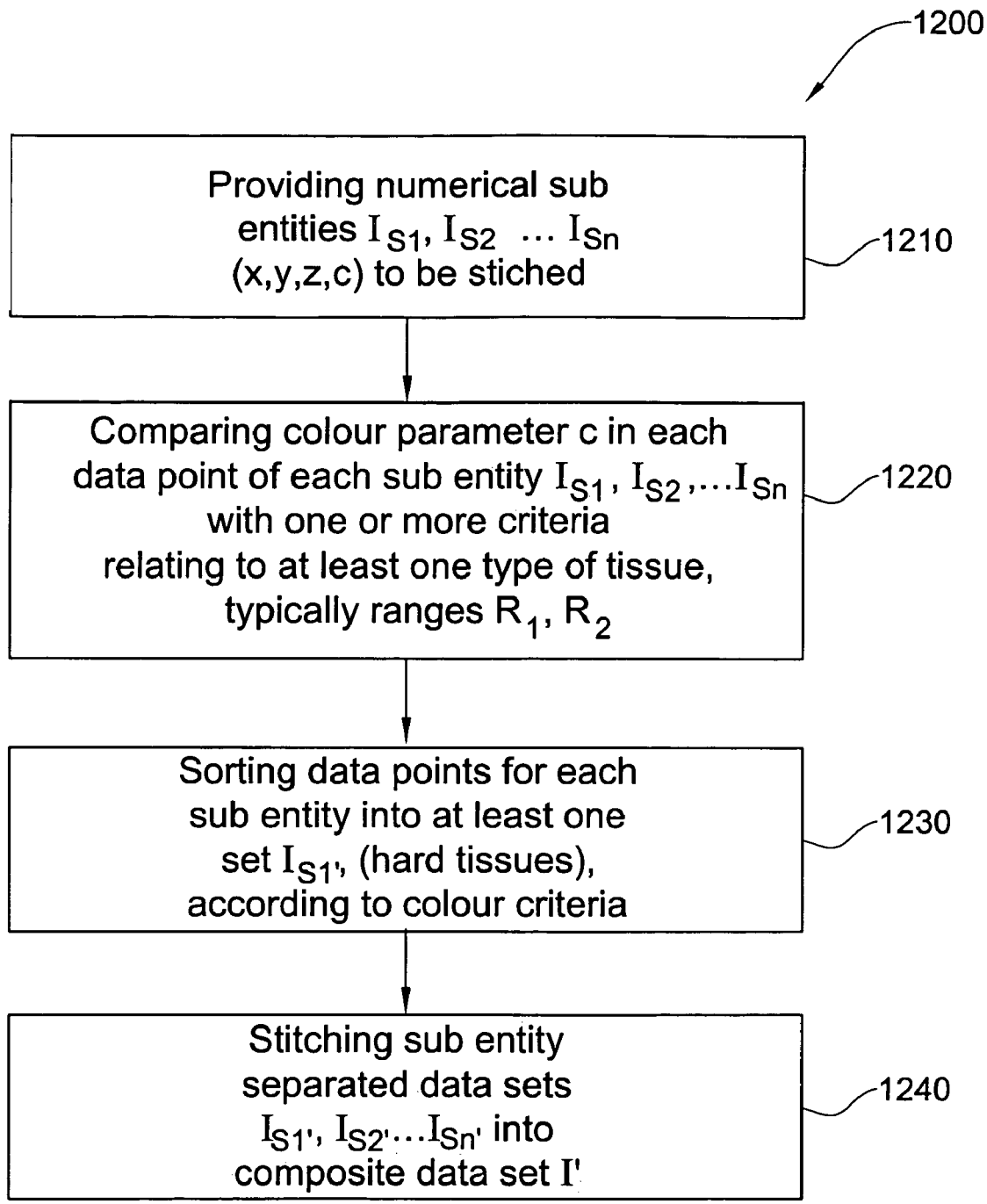
FIG. 15 illustrates the main steps of the method according to the second embodiment of the present invention.

In the second embodiment of the present invention, and referring to FIG. 15, the method, generally designated 1200, finds particular use for accurately stitching data sets of overlapping areas scanned within the intra-oral cavity. In the first step 1210, a suitable scanner, as described herein, for example, may be used for obtaining high resolution numerical sub-entities ($IS_1, IS_2, \ldots IS_n$) representative of the surface topography and color of zones ($A_1, A_2, \ldots A_n$) within the intra-oral cavity. The zones that are scanned should together fully span the target zone of interest. Some of these zones may overlap with all the other zones, while other zones may only overlap with one or two other zones, and thus theoretically the corresponding entities should have a portion of their data identical to one another within the overlap zone. However, since the scanner itself moves in orientation and position from scan to scan, the coordinates relating to these overlap zones will usually vary between adjacent scans, even though they relate to the same spatial feature. Nevertheless, by identifying the overlap zone within the entities, the spatial relationship between the entities may be established, and the various entities stitched together or combined to form a global numerical entity that comprises the full geometry and color representation of the target zone. The larger the overlap zone, the greater the accuracy with which the different zones may be synchronized together spatially.

In prior art methods, the overlap zones may be identified by numerically transforming the coordinates of an entity associated with one zone—by a series of translations and rotations—and in each case comparing the data set with the data set of another entity. This process is repeated until at least a portion of the data from the first entity coincides with at least a portion of the data from another entity. At this point, the data sets comprising the two sub-entities can be combined by adding both sets of coordinates, and discarding every data point that is repeated. However, some ambiguity may occur when using such a technique if a part of the intra-oral cavity (corresponding to part of the overlapping scanned data in some of the entities) moves in relation to other parts. For example, between one scan and another scan, part of the cheek may move relative to the teeth. It is then problematic to construct a composite entity comprising both scans since at least a part of the tissues (in this example the cheek) will be associated with two different data portions representative of the relative movement between scans.

In the second embodiment of the present invention, a method for stitching different data sets for the intraoral cavity is provided, in which the actual stitching technique is applied to data points corresponding to the hard tissues therein. Accordingly, in a second step 1220 of the method, the hard tissues including the teeth, fillings and prostheses are differentiated from the soft tissues including the gums, cheeks, lips and tongue. Substantially the same method as described above for first embodiment of the invention above may be utilized to identify the data, in each of the sub-entities ($IS_1, IS_2, \ldots IS_n$) that is associated with the hard tissues, mutatis mutandis. The data in these entities not corresponding to the hard tissues may de discarded or simply noted and set aside for future reference, thereby providing modified entities ($IS'_1, IS'_2, \ldots IS'_n$) comprising the data of interest relating to the hard tissues, for example.

In the next step 1230 of the method, the modified entities ($IS'_1, IS'_2, \ldots IS'_n$) are then manipulated in a similar manner in which the original entities ($I_1, I_2, \ldots I_n$) are manipulated in the prior art, mutatis mutandis, to register and then stitch the various modified entities ($IS'_1, IS'_2, \ldots IS'_n$) together to provide a composite entity I' that comprises the data points corresponding at least to the hard tissues.

As an optional step, the data referring to the soft tissues may then be added to the composite entity I' as follows. Referring to the soft tissue data corresponding to each scan as entities ($IS''_1, IS''_2, \ldots IS''_n$), each one of these entities is first manipulated in precisely the same manner as the corresponding entity of the group of modified entities ($IS'_1, IS'_2, \ldots IS'_n$) was manipulated in order to stitch the latter together into I'. After this, the coordinates of each pair of entities within the group ($IS''_1, IS''_2, \ldots IS''_n$) are compared in turn. Each pair of entities within the group ($IS''_1, IS''_2, \ldots IS''_n$) is checked to determine whether there exist some data points in one entity having two coordinates, say (x, y) identical to corresponding data points in the other entity, but in which the (z) coordinates are different All such data points in either one or the other entity are then disregarded. In this manner, a composite entity I'' can be constructed for the soft tissues, which can then be added to, if desired to the composite entity I' of the hard tissues previously created.

Typically, course stitching of the original sub entities ($IS_1, IS_2, \ldots IS_n$) is first carried out, and when the approximate relationships between the sub entities is known, a next step is performed, comprising fine stitching the corresponding separated hard-tissue sub entities ($IS'_1, IS'_2, \ldots IS'_n$).

Figure 16:
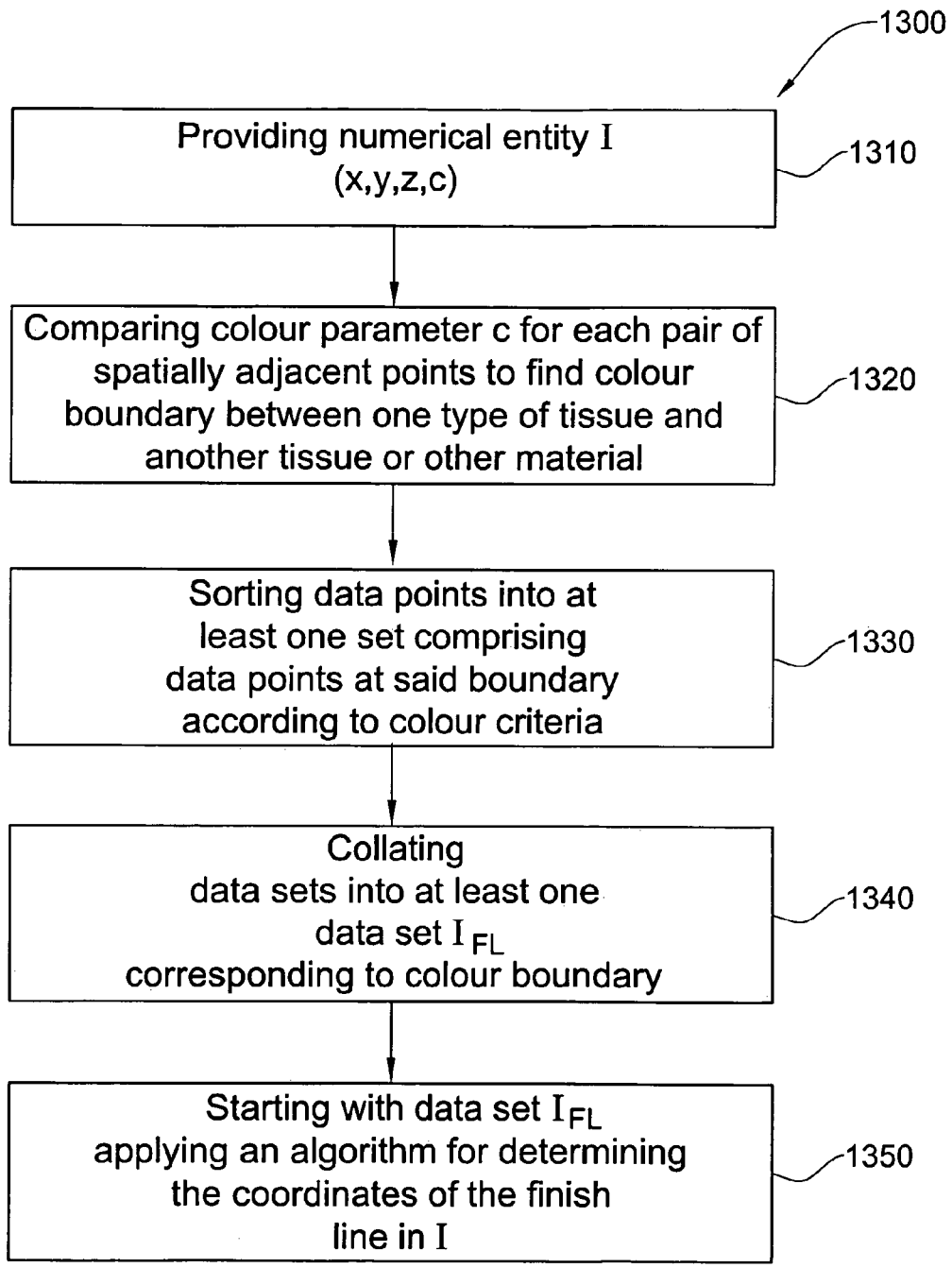
FIG. 16 illustrates the main steps of the method according to the third embodiment of the present invention.

In the third embodiment of the present invention, and referring to FIG. 16, the method, generally designated 1300, is used for automatically defining the finish line of a preparation. As described above, the finish line may be regarded as the circumferential junction or shoulder between the upper prepared portion of the tooth and the lower unprepared portion of the tooth. The finish line may be above or below the visible gum line, i.e. the exterior visible line of gingival tissue which circumferentially surrounds the tooth. In cases where the finish line protrudes from the gum, the complete circumferential extent of the finish line is visible and appears as a shade of white. This may be contrasted with the pink/red color of the surrounding gums, and at the same time the finish line is assumed to be in close proximity to the gums. In such a case, the method of the invention according to the third embodiment is carried out as follows.

As with other embodiments, the first step 1310 is to provide a numerical entity I that describes the target area—in this case the part of the intraoral cavity is that comprises the finish line—geometrically and with respect to color. Preferably, the target area is confined to the tooth having the preparation, and possibly the adjacent teeth. Then, in step 1320, an algorithm is applied to every pair of spatially adjacent data points, for example, wherein the value of the color parameter c of each of these points are compared one with the other, or with respect to some color criteria. When it is determined that the difference in color values is greater than a predetermined threshold, it is then assumed that the pair of data points are on opposite sides of a boundary between two tissues of different color, in particular between the edge of the tooth and the gum. Alternatively, the value of parameter c is compared with two predetermined ranges, $R_1$, $R_2$, wherein each range corresponds to a color associated with one or the other of teeth and gums. Then, wherever there is a pair of adjacent data points in which one data point has a value for parameter c within $R_1$ and the other data point has a value for parameter c within $R_2$, once again these two data points are considered to be on either side of the boundary between a tooth and the gum. The process is repeated for each adjacent pair of points in the entity I, thereby providing in step 1330 another numerical entity $I_{FL}$ representative of the gum line and comprising topographic (as well as color) information relating thereto.

Identification of the gum line itself provides a useful starting point for suitable algorithms that are then applied in step 1340 to determine the location and geometry of the finish line. Such algorithms typically attempt to identify features commonly found with finish lines, as has been described herein for the first embodiment. Thus, the algorithm is applied to the entity I, but staring with the surface data thereof corresponding to entity $I_{FL}$.

In cases where the finish line is partially or fully located below the gum, a suitable ring may be placed between the neck of the tooth preparation and the gum such as to retract the latter and expose the finish line. The method according to the third embodiment may then be applied with a modification in that the boundary between the tooth material and the ring material is searched for, in a similar manner to that described regarding the boundary between the tooth material and gum, mutatis mutandis, which provides a starting point for algorithms that are then applied to identify the finish line.

Preferably, where the entity I is viewable as a two dimensional color image on a screen, the method optionally further comprises the step of displaying on such an image of the entity I the finish line entity $I_{FL}$, preferably in a color having high contrast with respect to I, to enable the practitioner to check the result.

The method according to this embodiment may be modified to separate the soft tissues from the hard tissues, once the demarcation line between the two tissues is known, as determined above.

Figure 17:
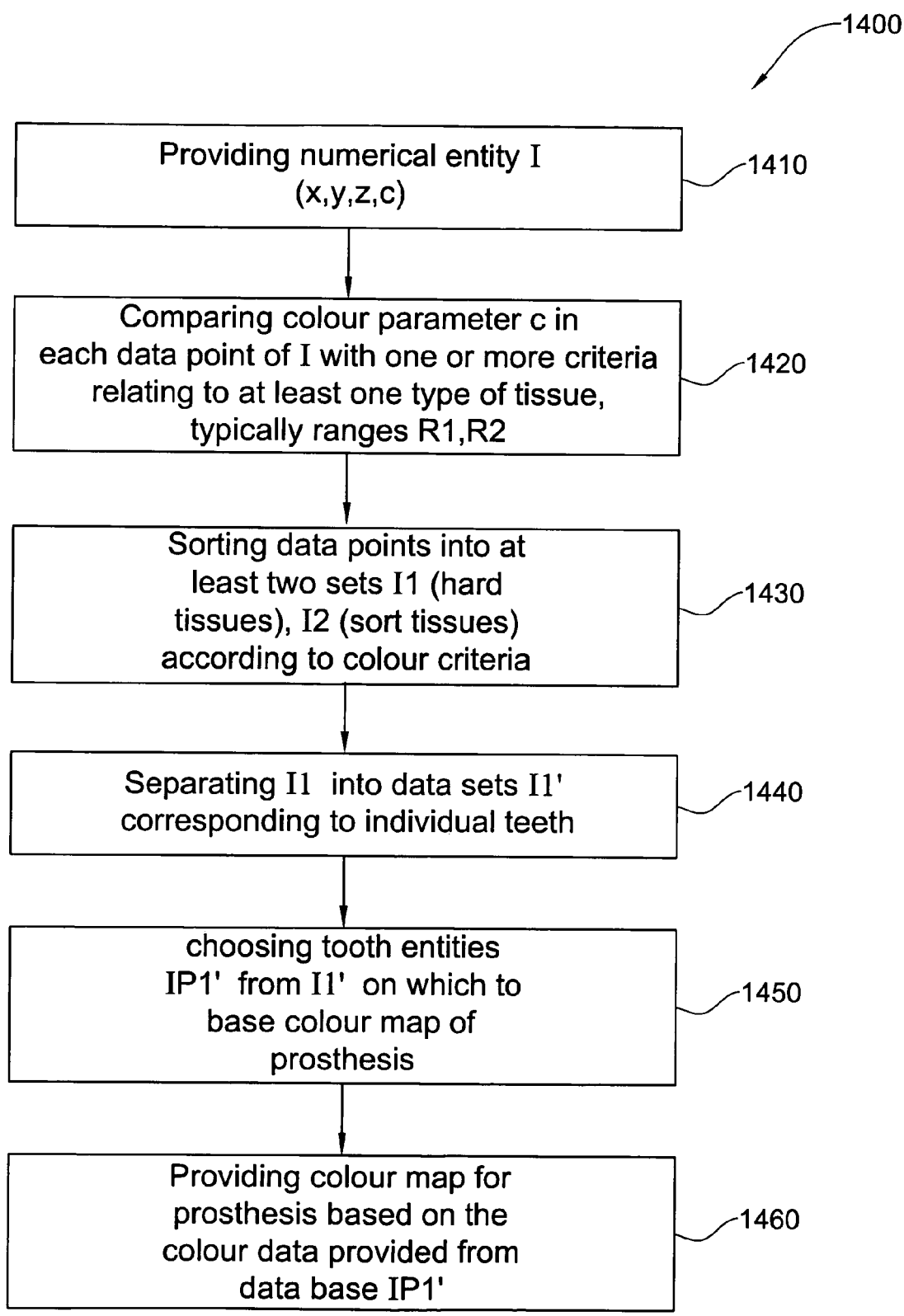
FIG. 17 illustrates the main steps of the method according to the fourth embodiment of the present invention.
Figure 18:
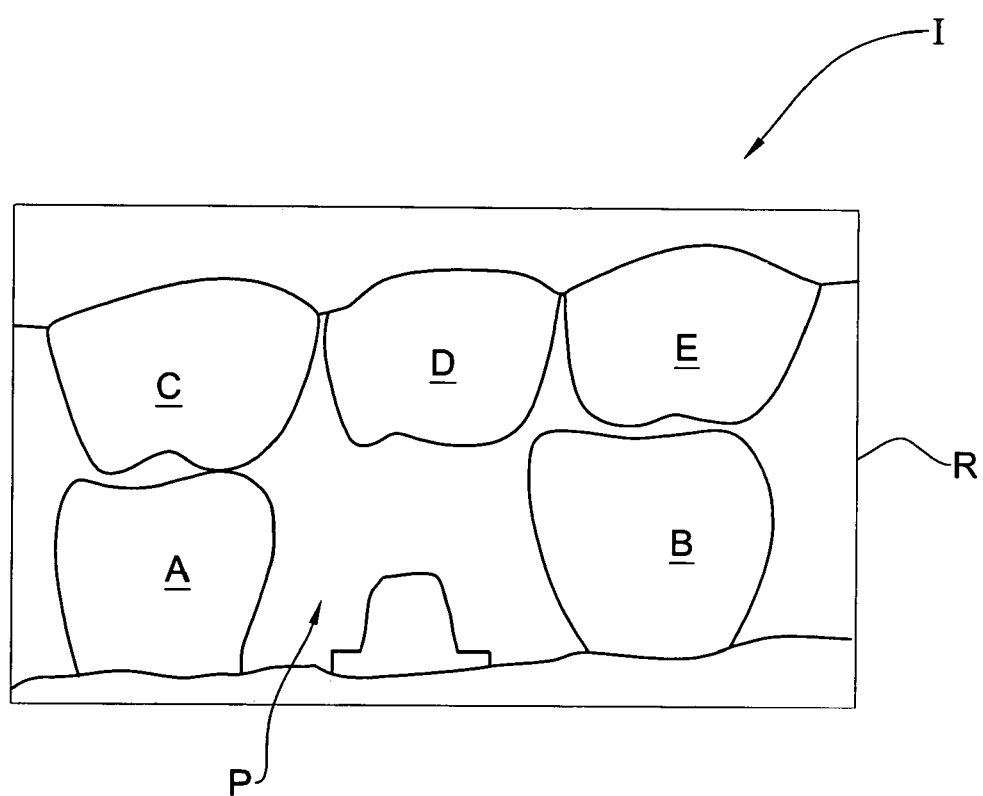
FIG. 18 illustrates a portion of the intraoral cavity on which it is desired to implant a dental prosthesis.

In the fourth embodiment of the invention, and referring to FIG. 17, the method, generally designated 1400, is particularly applied to the shading of a prosthesis. As with the other embodiments of the invention, the first step 1410 involves the creation of a numerical entity I of the region of interest within the oral cavity. Referring to FIG. 18, in this case, the region of interest R includes the preparation area P of the intraoral cavity in which the prosthesis is to be mounted, including adjacent teeth thereto, A, B as well as the teeth C, D, E opposite thereto on the opposing jaw. The region of interest R may optionally or alternatively include at least one tooth or teeth on the other side of the same jaw corresponding to the tooth or teeth that the prosthesis is designed to replace. The desired data in this embodiment that it is desired to create from the entity I relates to shading information for the prosthesis such as to provide a natural-looking appearance thereto that is compatible with the other teeth of the patient. The shading characteristics of the prosthesis according to the invention are to be based on the shading characteristics of at least one tooth of the patient, and thus share the same color, variations in hue and other features such as reflective qualities and translucency, that may be found on one or more teeth of the patient, according to any desired set of rules or algorithm.

In the next steps 1420, 1430, 1440, the entity I is manipulated such as to extract the data corresponding to the teeth only, and to separate this data into a set of discrete entities $I_1$, each of which represents an individual teeth, substantially as described regarding steps 1120, 1130 and 1140, respectively, for the first embodiment herein, mutatis mutandis.

Then, in step 1450, the decision is taken regarding which teeth are to be considered for modelling the shading of the prosthesis thereon. This decision may be made automatically, for example including only the adjacent teeth A, B, or the tooth D directly opposite the preparation area P, or any other appropriate tooth or combination of teeth. A suitable algorithm may be provided that recognizes which entity in $I_1$, corresponds to the area P, for example by determining the height of each tooth entity, and working out the entity having the shortest height. The height of each tooth may be obtained from the corresponding entity $I_1$, by suitable algorithms and routines, as known in the art. The spatial relationship between the entity corresponding to the area P and the entities corresponding to the other teeth can then be determined in an automated manner by using simple geometrical rules.

Alternatively, the choice may be made manually, and this may be done, for example, by displaying the scanned and separated teeth entities on a suitable display, such as a computer screen for example, and then marking the desired tooth or teeth by means of a cursor or the like. It may be preferable to manually perform this selection, as it would be important not to include certain teeth with particular visual defects or irregularities, e.g. cavities, parts that require restorations, spots that need to be removed etc. that it is not wished to repeat in the prosthesis.

The data sets $I_{P1'}$ corresponding to the chosen teeth are then analysed in turn, and in step 1460 a color map for the prosthesis is provided based on the color data provided from data base $I_{P1'}$.

Figure 19:
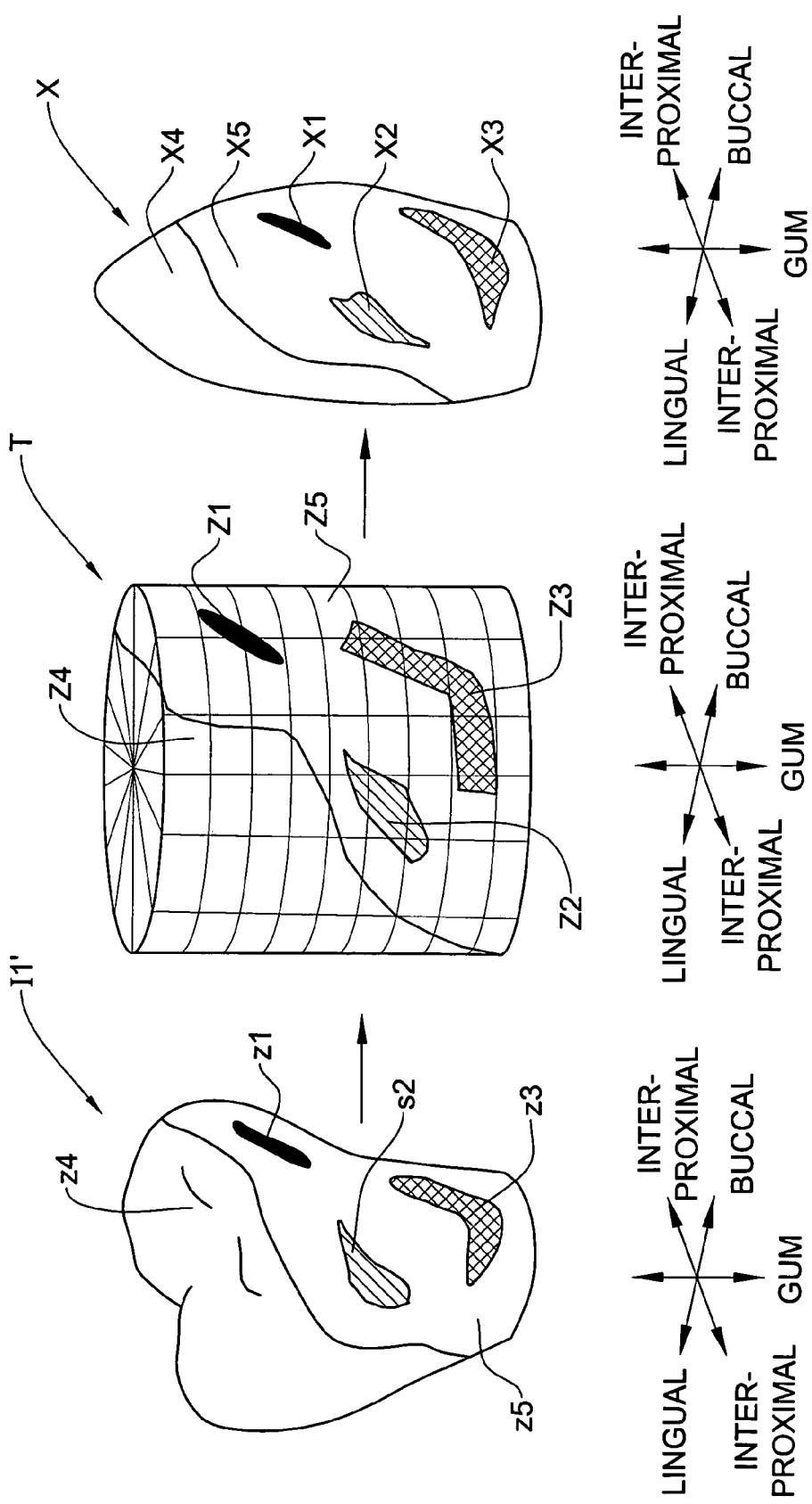
FIG. 19 schematically illustrates a transformation step according to the method of FIG. 17.

Referring to FIG. 19, for each of the teeth chosen, the appropriate entities are each geometrically transformed to conform to a predetermined geometrical shape, for the sake of example illustrated in this figure as a cylinder, to provide a transformed entity T. In the transformation process, the surface geometry of $I_{P1'}$ is transformed into the surface geometry of T, and the values of the color parameters c associated with every data point are correspondingly transferred. Effectively, then, the color attributes of each individual entity $I_{1'}$, such as for example features z1, z2, z3, and the two differently colored zones z4, z5 exemplified in FIG. 19, are thus mapped onto the entity T into areas Z1, Z2, Z3, Z4 and Z5 respectively.

When only one tooth is chosen for basing the shading of the prosthesis on, i.e., corresponding to only a single entity $I_{P1'}$, the transformed entity T thus obtained is then transformed again to assume the shape of the prosthesis, providing a prosthesis entity X, effectively mapping all the color features of the entity $I_{P1'}$ thereto. The shape of the prosthesis is previously determined by any suitable means, and this does not form part of the present invention. The entity X thus comprises the surface geometry of the prosthesis, and the shading information with respect to this geometry, including features x1-x5 transferred from features Z1-Z5 respectively, that will provide a similar appearance to that of the tooth on which the color was modelled. In such a case, the intermediate step of transforming $I_{P1'}$ to T may be dispensed with, and thus the entity $I_{P1'}$ may be transformed directly into the form of the crown prosthesis, thereby providing the values for the color c thereof.

Nevertheless, the inclusion of intermediate entity T may be useful.

Optionally, the tooth may be divided into three general zones: a gingival zone close to the gums, an intermediate body zone, and an incisal zone comprising the cusp of the tooth. The colors can be mapped into each of the zones independently, and then smoothed out between the zones to avoid sharp discontinuities in color.

When a number of teeth are chosen to serve as the basis for shading the prosthesis, the entities $I_{1'}$ corresponding to each of these teeth is transformed to a corresponding entity T'. Then, the color data of the entities T' are combined to provide a composite entity T of the same shape but having composite shading information obtained from all the entities $I_{1'}$. For example the color value at every geometrical point for all the entities T' could be averaged. Alternatively, a weighted average of the colors could be provided, wherein more weight is given to teeth that are closest in location and/or function than to other teeth. Again, when such a combination of the color information is effected, it is important to ensure that the various entities T' are aligned with respect to the individual interproximal, buccal and lingual sides. The composite entity T is then transformed geometrically to conform to the shape of the prosthesis to provide entity X as described before, but wherein the composite color values for parameter c are now transferred to the geometrical shape of the entity.

In the above example, the prosthesis has been exemplified as a crown. Nevertheless, the method may be applied to a bridge prosthesis, filing, restoration, or tooth transplant in a similar manner to that described, mutatis mutandis.

While the above embodiments have been described as operations carried out on discrete data points, it is clear that the method of the invention is applicable to similar operations being carried out on new data points suitably interpolated with respect to the original data points, mutatis mutandis.

Furthermore, it is also possible to carry out the method of the invention when the numerical entity is structured in a different manner to that described herein, mutatis mutandis. For example, rather than being described as a series of discrete data points on a surface, the surface of the intra-oral cavity could be described as a series of segments, by suitable formulae, or by any other geometric modelling method.

Figure 20:
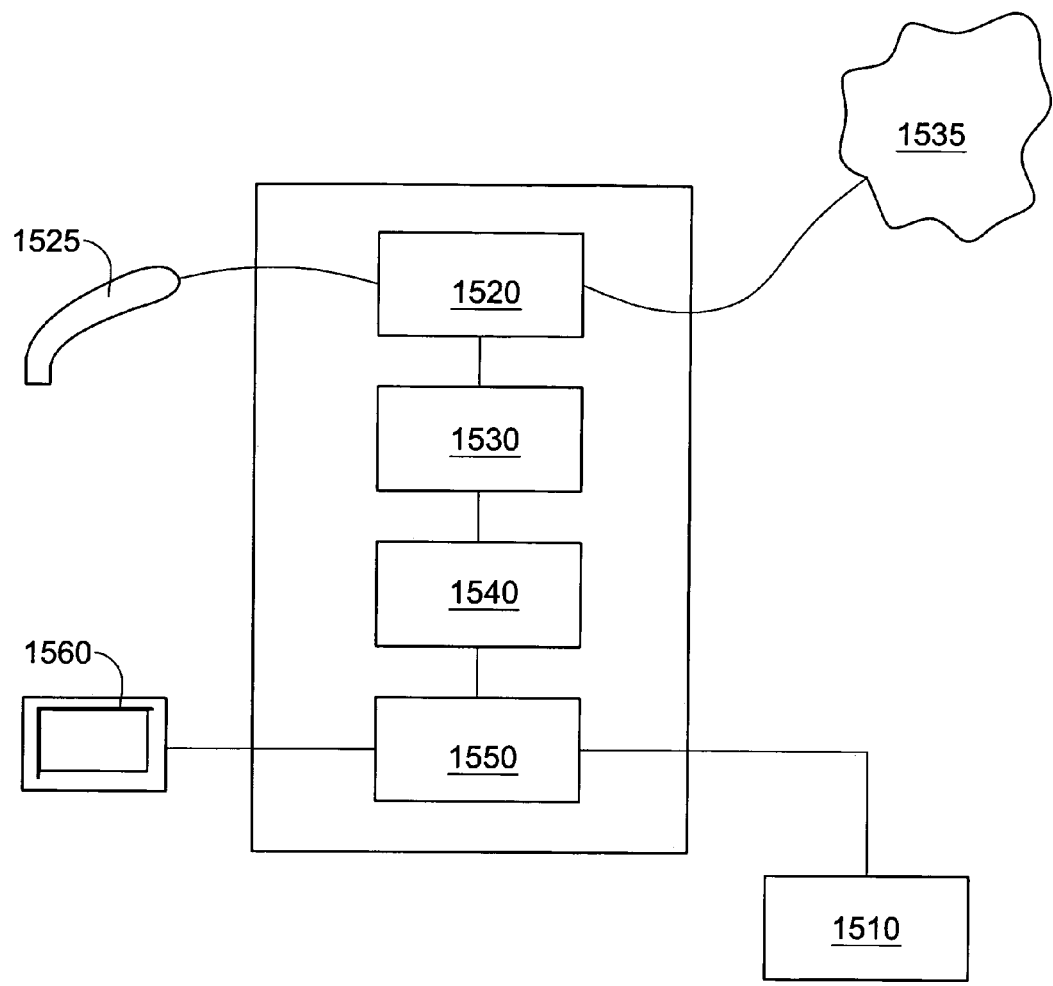
FIG. 20 is a block diagram of a system according to an embodiment of the present invention.

FIG. 20 is a block diagram of a system 1500 according to an embodiment of the present invention. System 1500 presents a software/hardware utility connectable to a virtual treatment system 1510, for example. System 1500 comprises such main elements as follows:

an input utility 1520 for receiving data indicative of three dimensional color data of the intra oral cavity, obtained directly using scanner 1525 (for example the device 100 described herein in reference to FIGS. 1 to 13) or obtained elsewhere and transmitted to the input facility via any communication medium 1535, including for example the internet, an intranet, and so on;

a memory utility 1530 for storing the data;

a processor utility 1540 for manipulating said first data set to provide desired data therefrom, particularly using any algorithm according to the present method; and output utility 1550.

System 1500 can be connected to a display 1560 or a printer (not shown) for visually presenting the manipulated entities. System 1500 can be also connectable to an additional utility such as a virtual treatment system 1510.

In another aspect of the present invention, a computer readable medium is provided that embodies in a tangible manner a program executable for providing data useful in procedures associated with the oral cavity. The computer readable medium comprises:

(a) a first set of data representative of the three dimensional surface geometry and color of at least part of the intra oral cavity;

(b) means for manipulating said first data set to provide desired data therefrom.

The medium may comprise, for example, optical discs, magnetic discs, magnetic tapes, and so on.

In the method claims that follow, alphabetic characters and Roman numerals used to designate claim steps are provided for convenience only and do not imply any particular order of performing the steps.

Finally, it should be noted that the word "comprising" as used throughout the appended claims is to be interpreted to mean "including but not limited to".

While there has been shown and disclosed exemplary embodiments in accordance with the invention, it will be appreciated that many changes may be made therein without departing from the spirit of the invention.

I claim:

1. A method of providing data useful in procedures associated with the oral cavity, comprising:

providing at least two numerical entities, each numerical entity being representative of a three-dimensional surface geometry and color of a corresponding part of the intra-oral cavity including at least a first tissue thereof, wherein each numerical entity comprises surface geometry data and color data associated with the respective corresponding part of the intra-oral cavity, and wherein said at least two numerical entities spatially overlap at respective overlap portions;

manipulating said at least two numerical entities to provide desired data therefrom; and (a) for each numerical entity providing at least one sub-entity comprising a first tissue data set exclusively comprising first surface geometry data and first color data corresponding to said first surface geometry data, wherein said first color data is correlated with a color representative of said first tissue, and wherein at least a first portion of said first surface geometry data corresponds to at least a part of the respective overlap portion of the respective numerical entity; and (b) stitching said at least two numerical entities together based on registering only said first portions of respective said first data sets.

2. The method according to claim 1, wherein said color data includes actual or perceived visual characteristics including one of more of hue, chroma, value, translucency, and reflectance.

3. The method according to claim 1, for differentiating said first tissue from a second tissue, wherein said first tissue comprises substantially different color characteristics from those of said second tissue, comprising separating said surface geometry data and said color data into at least two tissue data sets, wherein said first tissue data set comprises said first surface geometry data and said first color data, wherein said first color data is correlated with the color representative of said first tissue; and a second tissue data set comprises a second surface geometry data and a second color data, wherein said second color data is correlated with a color representative of said second tissue.

4. The method according to claim 3, wherein said first tissue and said second tissues comprise hard tissues and soft tissues, respectively, of the intra-oral cavity.

5. The method according to claim 4, wherein said first tissue comprises teeth.

6. The method according to claim 4, wherein said second tissue comprises at least one of gums, tongue, cheeks and lips.

7. The method according to claim 4, wherein said first tissue data set corresponds to a plurality of teeth of said intra-oral cavity.

8. The method according to claim 7, wherein said first tissue data set is divided into a plurality of sub data sets, wherein each said sub data set corresponds to a different tooth.

9. The method according to claim 8, further comprising the step of manipulating said sub data sets in a manner simulating an orthodontic treatment on said teeth.

10. The method according to claim 8, further comprising the step of displaying said sub data sets as images corresponding to individual teeth.

11. The method according to claim 1, further comprising the step of: for each entity separating said surface geometry data and said color data into a second tissue data set, comprising second surface geometry data and second color data, wherein said second color data is correlated with a color representative of a second tissue.

12. The method according to claim 11, wherein said second tissue comprises soft tissues of the intra-oral cavity.

13. The method according to claim 12, wherein said second tissue includes at least one of gums, tongue, cheeks and lips.

14. The method according to claim 1, wherein said first tissue comprises hard tissues of the intra-oral cavity.

15. The method according to claim 14, wherein said first tissue comprises teeth.

16. The method according to claim 1, wherein step (b) comprises: providing coarse stitching of the original numerical entities of step (a) by registering overlapping spatial data thereof to determine coarse spatial relationships between said numerical entities; applying said coarse spatial relationships to said first tissue data sets to facilitate registration of overlapping portions; and stitching said first tissue data sets together based on registering said overlapping portions.

17. The method according to claim 1, comprising using the color data associated with at least one tooth of said intra-oral cavity for providing shading data for a prosthesis for use in said intra-oral cavity.

18. The method according to claim 17, comprising: (a) providing separate numerical sub-entities each associated with a different one tooth within said intra-oral cavity; (b) providing a prosthesis entity comprising surface geometrical data, said prosthesis entity being associated with a desired prosthesis; (c) mapping color data from at least one sub entity in step (a) to said prosthesis entity according to predetermined criteria.

19. The method according to claim 18, wherein step (c) comprises (i) transforming the geometrical data of each said separate numerical sub-entities to correspond to a predetermined geometrical form, and mapping said color data to said geometrical form to provide for each said separate numerical sub-entity a transformed sub-entity; (ii) transforming the geometrical data in (b) to correspond to said prosthesis entity and mapping color data associated with the transformed sub-entity to said prosthesis entity.

20. The method according to claim 19, wherein in step (a) a plurality of separate numerical sub-entities associated with a corresponding plurality of teeth within said intra-oral cavity are provided; and wherein in step (c) the said transformed sub-entities are combined to a single transformed sub-entity, wherein color data corresponding to said plurality of numerical sub-entities in (a) are combined in a predetermined manner.

21. The method as claimed in claim 20, wherein said predetermined manner comprises averaging the color value at each corresponding data point of said plurality of numerical sub-entities in (a).

22. The method as claimed in claim 20, wherein said predetermined manner comprises weight averaging the color value at each corresponding data point of said plurality of numerical sub-entities in (a).

23. The method according to claim 18, wherein in step (a) a single numerical sub-entity associated with one tooth within said intra-oral cavity is provided.

24. The method according to claim 18, wherein step (a) comprises separating said surface geometry data and said color data into at least two tissue data sets, wherein said first tissue data set comprises said first surface geometry data and said first color data, wherein said first color data is correlated with the color representative of said first tissue; and a second tissue data set comprises second surface geometry data and second color data wherein said second color data is correlated with a color representative of said second tissue.

25. The method according to claim 24, wherein said first tissue and said second tissues comprise hard tissues and soft tissues, respectively, of the intra-oral cavity.

26. The method according to claim 25, wherein said first tissue comprises teeth.

27. The method according to claim 25, wherein said first tissue data set corresponds to a plurality of teeth of said intra-oral cavity.

28. The method according to claim 27, wherein said first tissue data set is divided into a plurality of sub-data sets, wherein each said sub-data set correspond to a different said tooth.

29. The method according to claim 1, for providing a finish line for a preparation area in said intra-oral cavity, comprising (a) comparing the color data for each pair of spatially adjacent data points in said numerical entity; (b) if the color data for said pair of data points are substantially different one from the other, providing one data point of said pair of data points; and (c) applying a search algorithm for identifying said finish line in said numerical entity, wherein said application of said algorithm is initially applied to a part of said numerical entity corresponding to the provided data points of step (b).

30. The method according to claim 29, wherein in step (b) the data point of said pair of data points having color data associated with a hard tissue is provided for step (c).

* * * * *